(12) United States Patent
Petit et al.

(10) Patent No.: US 9,795,679 B2
(45) Date of Patent: Oct. 24, 2017

(54) BIODEGRADABLE COMPOSITIONS SUITABLE FOR CONTROLLED RELEASE

(75) Inventors: Audrey Petit, Groningen (NL); Peter Bruin, Groningen (NL); Mike De Leeuw, Groningen (NL); Ronald Meijboom, Groningen (NL)

(73) Assignee: INGELL TECHNOLOGIES HOLDING B.V., Groningen (NL)

( * ) Notice: Subject to any disclaimer, the term of this patent is extended or adjusted under 35 U.S.C. 154(b) by 41 days.

(21) Appl. No.: 14/008,671

(22) PCT Filed: Apr. 2, 2012

(86) PCT No.: PCT/EP2012/055998
§ 371 (c)(1),
(2), (4) Date: Apr. 22, 2014

(87) PCT Pub. No.: WO2012/131106
PCT Pub. Date: Oct. 4, 2012

(65) Prior Publication Data
US 2015/0165042 A1    Jun. 18, 2015

(30) Foreign Application Priority Data
Mar. 31, 2011 (EP) .................................. 11002676

(51) Int. Cl.
| | |
|---|---|
| *A61K 8/00* | (2006.01) |
| *A61K 47/34* | (2017.01) |
| *A61K 9/00* | (2006.01) |
| *A61K 9/06* | (2006.01) |
| *A61K 49/04* | (2006.01) |
| *C08L 67/04* | (2006.01) |
| *C08G 63/664* | (2006.01) |
| *A61K 51/06* | (2006.01) |
| *A61K 47/30* | (2006.01) |
| *A61K 47/10* | (2017.01) |

(52) U.S. Cl.
CPC ............ *A61K 47/34* (2013.01); *A61K 9/0019* (2013.01); *A61K 9/0024* (2013.01); *A61K 9/06* (2013.01); *A61K 49/0438* (2013.01); *A61K 49/0442* (2013.01); *A61K 49/0457* (2013.01); *A61K 51/065* (2013.01); *C08G 63/664* (2013.01); *C08L 67/04* (2013.01); *A61K 47/10* (2013.01); *A61K 47/30* (2013.01)

(58) Field of Classification Search
None
See application file for complete search history.

(56) References Cited

U.S. PATENT DOCUMENTS 5,702,717 A * 12/1997 Cha ...................... A61K 9/0024
424/424
2005/0036946 A1 2/2005 Pathak et al.
2007/0265356 A1 11/2007 Kim et al.

FOREIGN PATENT DOCUMENTS

| CN | 101862454 A | 10/2010 |
|---|---|---|
| EP | 0 863 745 B1 | 5/2004 |
| WO | 00 18821 A1 | 4/2000 |
| WO | 00 38651 A1 | 7/2000 |
| WO | 01 82970 A1 | 11/2001 |

OTHER PUBLICATIONS

Yu, L., et al., Mixing a Sol and a Precipitate of Block Copolymers with Different Block Ratios Leads to an Injectable Hydrogel, Biomacromolecules 2009, 10, pp. 1547-1553, XP-002586070.
Jo, S., et al, Reverse Thermal Gelation of Aliphatically Modified Biodegradable Triblock Copolymers, Macromol. Biosci., 2006, pp. 923-928.

* cited by examiner

*Primary Examiner* — James Rogers
(74) *Attorney, Agent, or Firm* — Hudak, Shunk & Farine Co. LPA

(57) ABSTRACT

Simple mixing/blending of a special class of drug-depot forming tri-block copolymers polymers, with the opportunity to cost-effectively tailor drug delivery performances of such biodegradable, injectable depots in a clinical and an industrial setting. How to visualize these depots for various imaging related purposes is described. A composition comprising (a) an active ingredient, preferably a pharmaceutically active ingredient (b) a solvent and (c) a mixture of at least two types of tri-block copolymers of formula (1)

$$B\text{-}A\text{-}B \quad (1)$$

wherein B stands for a hydrophobic block and wherein A stands for a hydrophilic block, wherein the mixture is prepared by mixing at least two types of tri-block copolymers having a degree of modification of 100% and wherein the at least two types of B-A-B types of tri-block copolymers differ only on the type of end-group or wherein the mixture is prepared by mixing at least two types of tri-block copolymers, wherein one of the at least two tri-block copolymers has a degree of modification of 100% and one of the at least two tri-block copolymers has a degree of modification of 0% and wherein the at least two types of B-A-B types of tri-block copolymers differ only on the degree of modification of the end-groups.

16 Claims, 8 Drawing Sheets squares: DM2 triangles: DM1 circles: 1:1 mixture DM0 + DM2 diamonds: DM0

Polymer #17 (squares) ; #17/#81 (75/25) (open triangles)

BIODEGRADABLE COMPOSITIONS SUITABLE FOR CONTROLLED RELEASE

FIELD OF THE INVENTION

The invention relates to a composition comprising (a) a (pharmaceutically) active ingredient (b) a solvent and (c) a mixture of at least two types of biodegradable tri-block copolymers, to this composition for use as a medicament, a process for the preparation of said composition and to a method for delivering a (pharmaceutically) active ingredient over an extended period to an animal, including a human.

BACKGROUND OF THE INVENTION

In recent years, there has been considerable effort to provide systems that are capable of controlled release of drugs in animals, including humans. Some drugs can only be administered to a patient by injection. Controlled release of such drugs has the advantage that the patient does not need to be subjected to multiple injections, but instead only one or a few injections with the controlled release system would suffice.

Some injections into areas of the patient's body are (very) painful. Examples of such difficult to dose areas are the eyes, the (synovial) joints, the muscles or the spine. Injection with a drug in a controlled release system will limit the amount of injections needed and will enhance the chance that a patient will continue with the therapy. This will greatly increase the success of the treatment.

Controlled release systems that are very suitable for being injected into such difficult to dose areas are thermogels based on compositions comprising polymers. The polymers have the unique property that at low temperatures they are water soluble, whereas at higher temperatures the polymers form a gel. Preferably, for use as a system that is capable of controlled release, the polymer is soluble in the solvent used at room temperature (e.g. 21° C.) and forms a gel once injected into the body (temperature in the range from 30 to 42° C.).

A gel (or a hydrogel in the context of the present invention) is a network of polymer chains that are hydrophilic and contain a substantial amount of water (for example between 50 and 99% water, preferably between 66 and 85% water). The gel shows no flow in a vial tilt test: when a glass vial which contains the gel is turned upside down, no flow of the gel is observed during 15 seconds observation time.

Since different drugs require a different drug administration regime, there is a desire to make thermogels having a tunable release profile.

Methods to tune release profiles of thermogels of BAB-type tri-block copolymers have been described by Yu et al., in 'Mixing a sol and a precipitate of block copolymers with different block ratios leads to an injectable hydrogel' in Biomacromolecules, 2009, 10, 1547-1553 and in CN200910049664. Yu et al. describe a method to obtain a thermoreversible physical hydrogel by mixing an aqueous solution of an BAB-type triblock copolymer poly(D,L-lactic acid-c-glycolic acid)-b-polyethylene glycol-b-poly(D,L-lactic acid-co-glycolic acid), as indicated PLGA-PEG-PLGA, with a precipitate of a similar copolymer but with a different block ratio. According to Yu et al., this method provides a very convenient approach to design injectable thermogelling biomaterials with a broad adjustable window, which copolymer mixture platform can potentially be used in drug delivery.

Also, WO 01/82970 A1 discloses a water-soluble, biodegradable reverse thermal gelation system comprising a mixture of at least two types of tri-block copolymers. The drug release and gel matrix erosion rates of the mixture of copolymers may be modulated by various parameters such as the hydrophobic/hydrophilic component contents, polymer block concentrations, molecular weights and gelation temperatures, and weight ratios of the tri-block copolymer components in the mixture.

However, from a regulatory point of view, every time a different polymer is used in a thermogel blend, the new mixture needs to go through a new regulatory approval process before the national or regional drug approval authority (such as the Federal Drug Administration (FDA) in the US or its European equivalent the European Medicines Agency (EMEA) in Europe). This will prolong the very important time-to-market considerably.

SUMMARY OF THE INVENTION

Therefore, it is the object of the invention to provide compositions for which the release profile can easily be tuned, but which have a shorter time to market.

This object is achieved by a composition comprising (a) an active ingredient, preferably a pharmaceutically active ingredient (b) a solvent and (c) a mixture of at least two types of tri-block copolymers of formula (1)

$$B\text{-}A\text{-}B \tag{1}$$

wherein B stands for a hydrophobic block and wherein A stands for a hydrophilic block wherein the at least two types of B-A-B types of tri-block copolymers differ only on the type of end-group and/or on the degree of modification of the end-groups.

Preferably, the invention relates to a composition comprising (a) an active ingredient, preferably a pharmaceutically active ingredient (b) a solvent and (c) a mixture of at least two types of tri-block copolymers of formula (1)

$$B\text{-}A\text{-}B \tag{1}$$

wherein B stands for a hydrophobic block and wherein A stands for a hydrophilic block, wherein the mixture is prepared by mixing at least two types of tri-block copolymers having a degree of modification of 100% and wherein the at least two types of B-A-B types of tri-block copolymers differ only on the type of end-group or wherein the mixture is prepared by mixing at least two types of tri-block copolymers, wherein one of the at least two tri-block copolymers has a degree of modification of 100% and one of the at least two tri-block copolymers has a degree of modification of 0% and wherein the at least two types of B-A-B types of tri-block copolymers differ only on the degree of modification of the end-groups.

BRIEF DESCRIPTION OF THE DRAWINGS

The invention will be better understood and other features and advantages will become apparent by reading the detailed description of the invention, taken together with the drawings, wherein.

C6DM2/DM0 25/75: this is a blend of 25 wt % of a 20% w/w solution of tri-block copolymer II in PBS, pH 7.4 and 75 wt % of a 20% w/w solution of tri-block copolymer I in PBS, pH 7.4.

C6DM2/DM0 50/50: this is a blend of 50 wt % of a 20% w/w solution of tri-block copolymer II in PBS, pH 7.4 and 50 wt % of a 20% w/w solution of tri-block copolymer I in PBS, pH 7.4.

C6DM2/DM0 75/25: this is a blend of 75 wt % of a 20% w/w solution of tri-block copolymer II in PBS, pH 7.4 and 25 wt % of a 20% w/w solution of tri-block copolymer I in PBS, pH 7.4

C6DM2/DM0 100/0: this is a blend of 100 wt % of a 20% w/w solution of tri-block copolymer II in PBS, pH 7.4 and 0 wt % of a 20% w/w solution of tri-block copolymer I in PBS, pH 7.4

Figure 2:
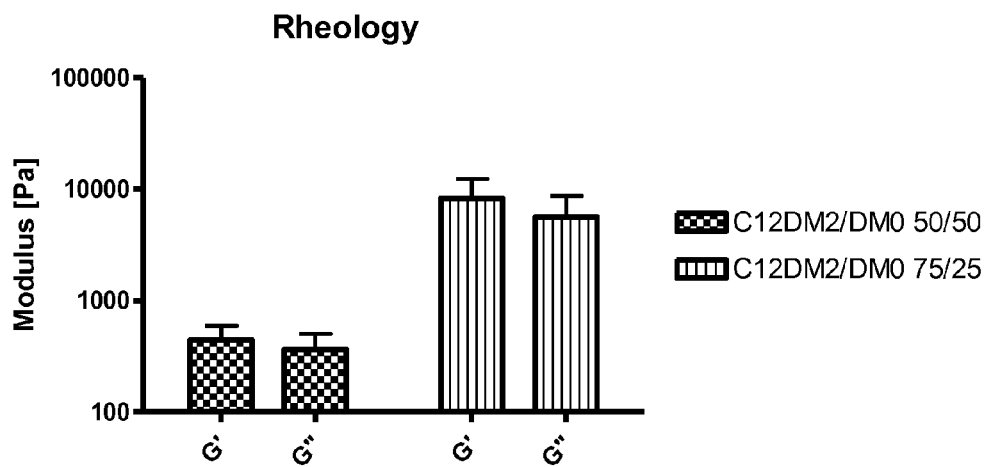

FIG. 2 shows the rheological properties at 37° C. of mixtures containing PLCA-PEG-PLCA and PLCA-PEG-PLCA laurate. Gels were 20% (w/w). Measurement frequency and strain were 1 Hz and 1%, respectively. Error bars represent standard deviation (n=3).

In FIG. 2, the following abbreviations are used:
C12DM2/DM0 50/50: this is a blend of 50 wt % of a 20% w/w solution of tri-block copolymer III in PBS, pH 7.4 and 50 wt % of a 20% w/w solution of tri-block copolymer I in PBS, pH 7.4

C12DM2/DM0 75/25: this is a blend of 75 wt % of a 20% w/w solution of tri-block copolymer III in PBS, pH 7.4 and 25 wt % of a 20% w/w solution of tri-block copolymer I in PBS, pH 7.4

Figure 3:
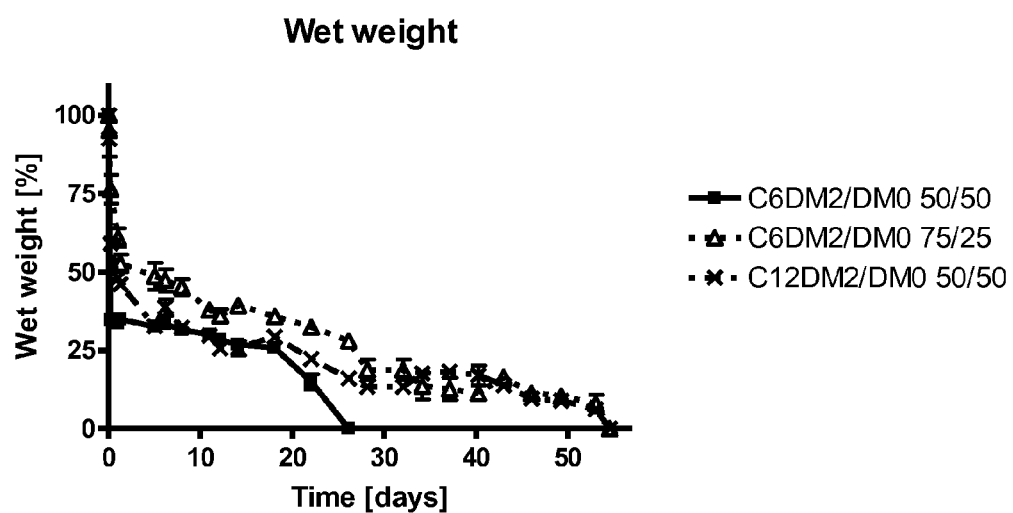

FIG. 3 shows the weight change of the different gels, i.e. degradation over time of mixtures in PBS, pH 7.4, 37° C. containing 0.2% Tween 80 (+0.02% NaN3). Gels were 20% (w/w) containing 0.5% Celecoxib wrt polymer. Error bars represent standard deviation (n=3).

In FIG. 3, the following abbreviations are used:
C6DM2/DM0 75/25: this is a blend of 75 wt % of a 20% w/w solution of tri-block copolymer II in PBS, pH 7.4 and 25 wt % of a 20% w/w solution of tri-block copolymer I in PBS, pH 7.4

C6DM2/DM0 50/50: this is a blend of 50 wt % of a 20% w/w solution of tri-block copolymer II in PBS, pH 7.4 and 50 wt % of a 20% w/w solution of tri-block copolymer I in PBS, pH 7.4.

C12DM2/DM0 50/50: this is a blend of 50 wt % of a 20% w/w solution of tri-block copolymer III in PBS, pH 7.4 and 50 wt % of a 20% w/w solution of tri-block copolymer I in PBS, pH 7.4

Figure 4:
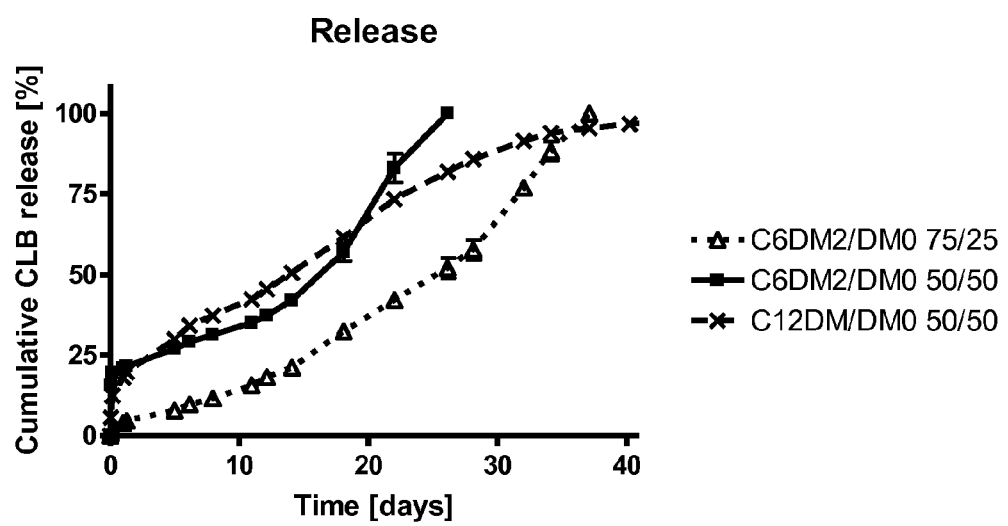

FIG. 4 shows the cumulative release of celecoxib from the different gels over time of mixtures in PBS, pH 7.4, 37° C. containing 0.2% Tween 80 (+0.02% NaN3). Gels were 20% (w/w) containing 0.5% celecoxib wrt polymer. Error bars represent standard deviation (n=3).

In FIG. 4, the following abbreviations are used:
C6DM2/DM0 50/50: this is a blend of 50 wt % of a 20% w/w solution of tri-block copolymer II in PBS, pH 7.4 and 50 wt % of a 20% w/w solution of tri-block copolymer I in PBS, pH 7.4.

C6DM2/DM0 75/25: this is a blend of 75 wt % of a 20% w/w solution of tri-block copolymer II in PBS, pH 7.4 and 25 wt % of a 20% w/w solution of tri-block copolymer I in PBS, pH 7.4

C12DM2/DM0 50/50: this is a blend of 50 wt % of a 20% w/w solution of tri-block copolymer III in PBS, pH 7.4 and 50 wt % of a 20% w/w solution of tri-block copolymer I in PBS, pH 7.4.

Figure 5:
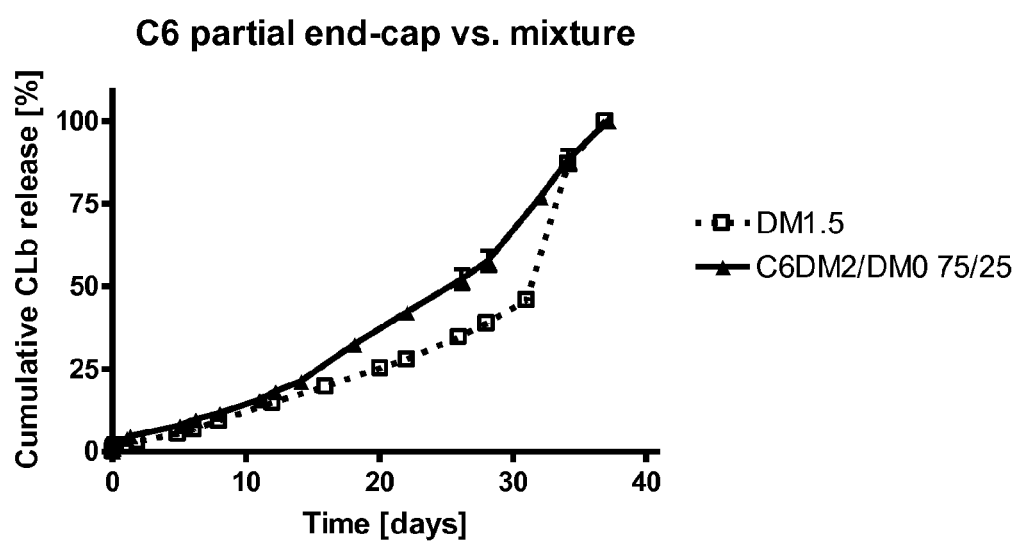

FIG. 5 shows the cumulative release of celecoxib over time of the partially C6-modified PLCA-PEG-PLCA (DM 1.5) in PBS, pH 7.4, 37° C. containing 0.2% Tween 80 (+0.02% NaN3). Gels were 20% (w/w) containing 0.5% celecoxib wrt polymer. Error bars represent standard deviation (n=3).

In FIG. 5, the following abbreviations are used:
DM 1.5: this is a blend of 100 wt % of a 20% w/w solution of tri-block copolymer IV in PBS, pH 7.4 and 0 wt % of a 20% w/w solution of tri-block copolymer I in PBS, pH 7.4.

C6DM2/DM0 75/25: this is a blend of 75 wt % of a 20% w/w solution of tri-block copolymer II in PBS, pH 7.4 and 25 wt % of a 20% w/w solution of tri-block copolymer I in PBS, pH 7.4.

Figure 6:
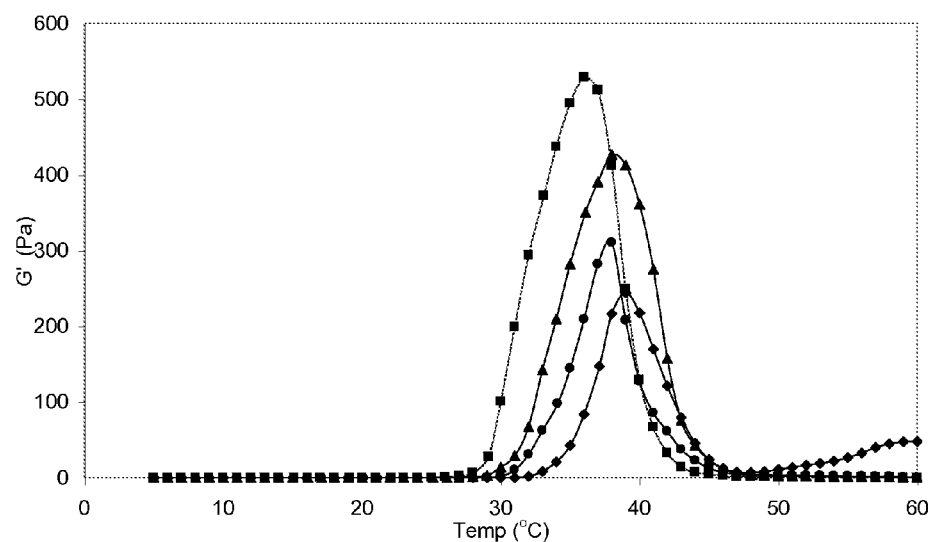

FIG. 6 shows the rheological properties of compositions containing PLGA-PEG-PLGA with or without acylation, and mixtures thereof. Gels were 20% (w/w). Measurement frequency and strain were 1 Hz and 1% respectively.

In FIG. 6 the following abbreviations are used:
DM0: PEG1500(GLY33%/LAC67%)2
DM1: PEG1500(GLY33%/LAC67%)2(C2)1
DM2: PEG1500(GLY33%/LAC67%)2(C2)2
1:1: mixture of DM0 and DM2 in ratio of 1 to 1

Figure 7:
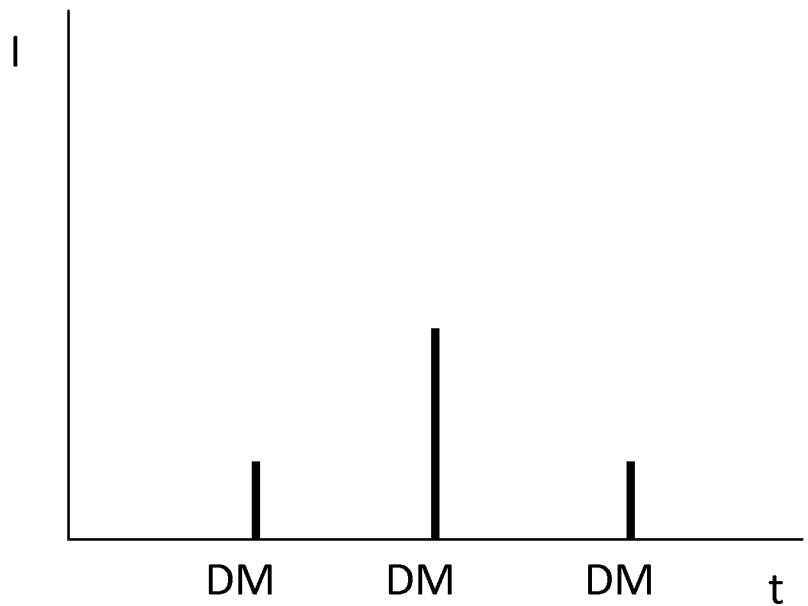

FIG. 7 shows a postulated elution profile where t=time and I=Intensity, for a composition consisting of 100% DM1.

Figure 8:
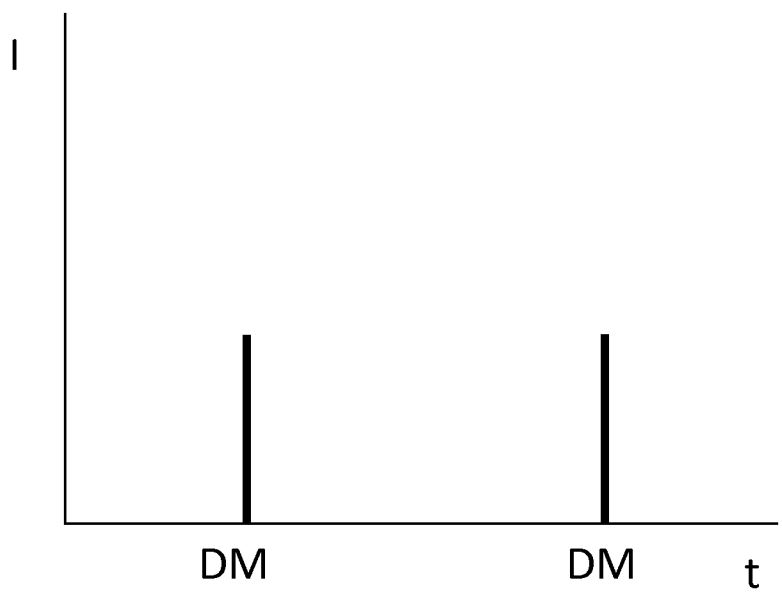

FIG. 8 shows a postulated elution profile for a composition consisting of a 50/50 mixture of tri-block copolymer having a DM of 0 and a tri-block copolymer having a DM of 2.

Figure 9:
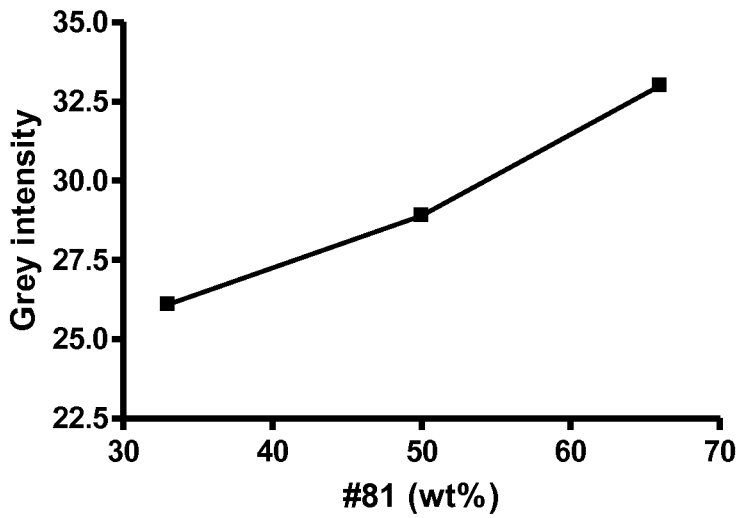

FIG. 9 shows the x-ray intensities as measured by the microCT, for compositions shown in Table 10, example 16, whereby the percentage of iodine bound polymer P(#81) is given on the x-axis. The line is added to guide the eye.

Figure 10A:
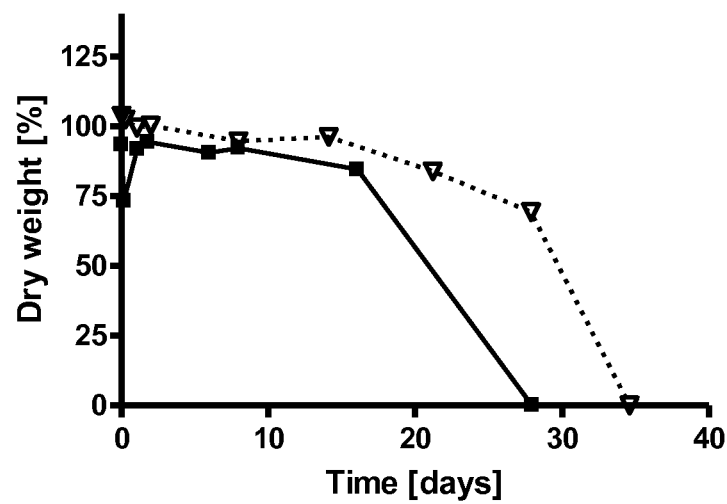
Figure 10B:
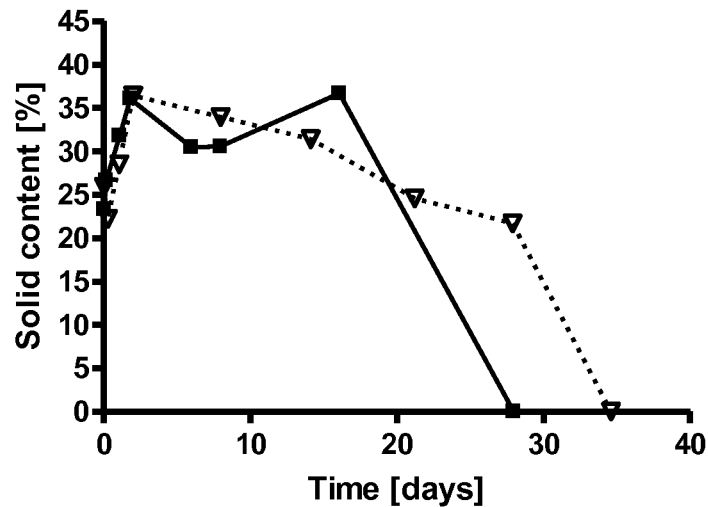
Figure 10C:
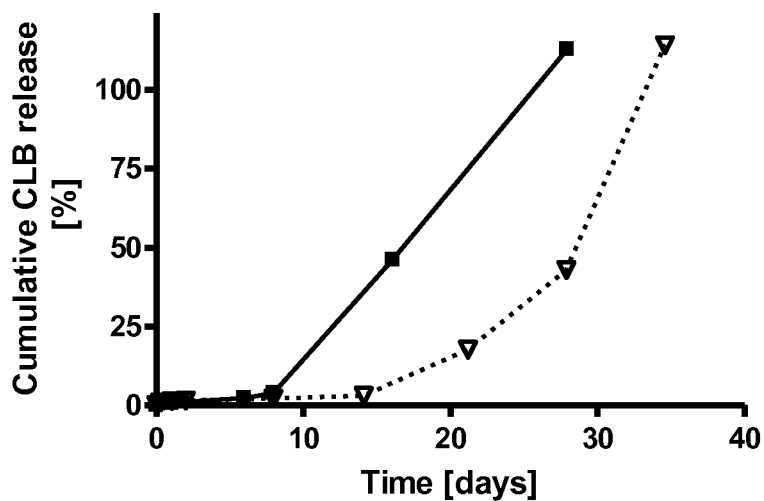
Figure 10D:
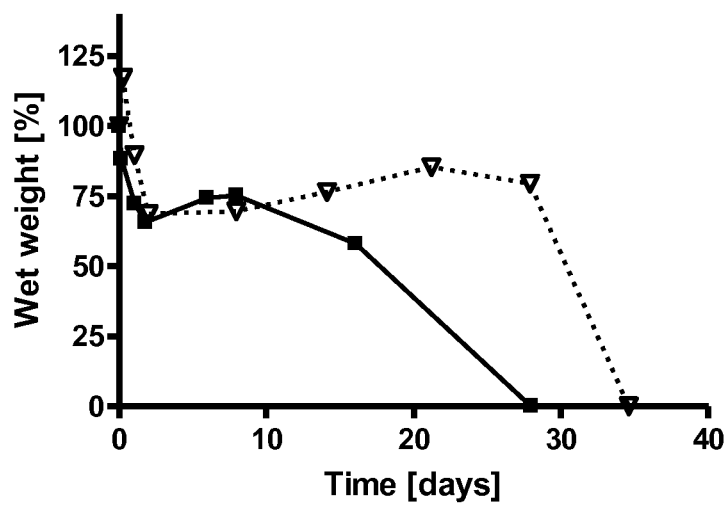

FIGS. 10 a-c show the release profile and gel erosion profiles for example 18, dry weight in FIG. 10a, solid content in FIG. 10b and cumulative CLB release in FIG. 10c. The filled squares indicate composition 18a (OAc-Gell only loaded with Celecoxib) and the empty triangles indicate composition 18b (OAc-Gell/I-GellΩ#1-#81). The compositions contained 25 wt % in 50 mM phosphate buffer, pH 7.4, 0.42% NaCl and 0.05% NaN3. The loading of Celecoxib was 1.25 mg/mL.

Figure 11:
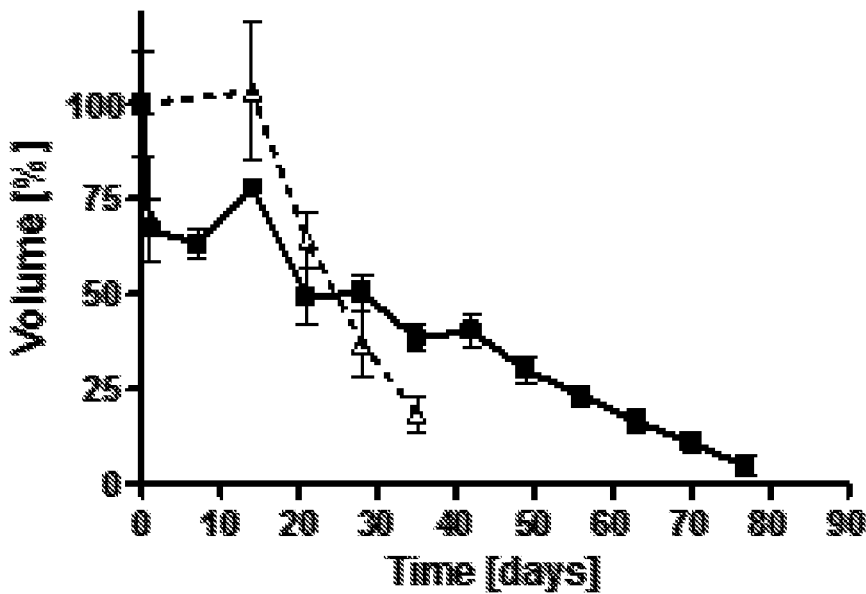

FIG. 11 shows the erosion profile for compositions 19a (dotted line) and 19b (Solid line). Images of the subcutaneous injected I-Gell depots in rats were taken in-vivo using micro-CT on days 0-1-4-8-14-21-28-35-42-49-56-63-70-77 and the volume of the gel was determined using a caliper as done routinely for volume-estimations of subcutaneous tumor lumps.

DETAILED DESCRIPTION OF THE INVENTION

By varying the choice and amount of end-groups of the BAB-type tri-block copolymers that are present in the composition of the present invention, the release profile for a drug can easily be varied. Furthermore, since the BAB-type tri-block copolymers of the composition of the invention have the same backbone and only differ in the choice or amount of end-groups, the regulatory approval process of the composition can be considerably shortened if not completely skipped. The composition of the present invention is therefore very suitable for the controlled release of different types of drugs, the release profile of which can be easily varied and adapted to the drug used.

For the avoidance of doubt, the terms 'pharmaceutically active ingredient' and 'drug' are used interchangeably herein.

A further advantage of the composition of the present invention is that the preparation of the tri-block copolymers is much easier. In case of the tri-block copolymers of the invention, the synthesis of the tri-block copolymer having hydroxyl end-groups can be standardized. End-group modification (amount and/or degree) can then be done on the same batch of standardized tri-block copolymer having hydroxyl end-groups.

In case of the tri-block copolymers used in the mixtures described in Yu et al., in 'Mixing a sol and a precipitate of block copolymers with different block ratios leads to an injectable hydrogel', Biomacromolecules, 2009, 10, 1547-1553 and in CN200910049664 and in WO01/82970 A1, every time a different set of tri-block copolymers needs to synthesized in order to be able to tune the release profile for a particular drug.

Furthermore, the compositions of the present invention may have various other advantage besides adaptability of the release profile of the compositions that can be prepared therewith, such as for example that it can provide compositions having variable stability, degradation time, gelling temperature, injectability/viscosity, storage modulus and/or loss modulus.

Furthermore, the composition of the present invention may be more stable than the known mix compositions, since the micelles in the thermogel, by or in which the (pharmaceutically) active ingredients are retained, are more homogeneous. Also, the stability of the active ingredient present in the composition of the invention may be tuned by the method of the invention.

Not only the release profile of the drug may be tuned by using the method of the invention, but also the solubility of the composition can be varied depending on the choice and amount of end-group modification. Solubility of the composition is an important parameter in the formulation of an injectable thermogel.

With 'hydrophilic block' is meant that the block by itself has a solubility in water of at least 0.8% by weight, preferably at least 1% by weight. For example PEG is a hydrophilic block.

With 'hydrophobic block' is meant that the block by itself has a solubility in water of at most 0.7% by weight, preferably less than 0.2% by weight. For example a copolyester block is considered to be hydrophobic.

Modification of the hydroxyl end-groups of the tri-block copolymers in the composition of the invention also offers the possibility to introduce multifunctionality. For example, the hydroxyl group of the tri-block copolymer may be modified with heteroatoms which might increase the affinity of the drug for the micelles (hydrogen bonds) or unsaturation (pi-pi interaction) and/or which are imagable, such as iodo groups, which can be imaged by X-ray or MRI, or may be modified with a compound that interacts with (and could also stabilize) the active ingredient or may be modified with cell-attracting moieties, such as the cell adhesive RGD peptide. The latter may provide a method for recruiting cells into/onto the thermogel after injection into the body.

Preferably, the invention relates to a composition of the invention wherein the end-group of at least one of the two types of tri-block copolymer is covalently bound to a compound containing radiopaque atoms, for example iodine or barium.

For example in case the endgroup is an acyl group, the acyl group may be substituted with a radiopaque atom, for example iodine. For example, an acyl group substituted with a radiopaque atom may be iodobenzoyl.

The radiopaque atoms may be visualized in situ using X-ray, for example 2D or 3D CT (X-ray computed tomography).

The invention therefore also relates to a composition comprising a tri-block copolymer according to formula (1)

B-A-B (1)

wherein A stands for a linear poly-(ethylene glycol) block and wherein B stands for wherein B stands for a poly (lactide-co-ε-caprolactone) block, wherein at least part of the hydroxyl end-groups of the tri-block copolymer are covalently bound to a compound containing radiopaque atoms.

Preferably, the radiopaque atom is iodine.

Preferably, said composition further comprises an active ingredient, preferably a pharmaceutically active ingredient and/or a solvent.

By including a pharmaceutically active ingredient in said composition, it is possible to correlate the degree of gel erosion with the degree of release of pharmaceutically active ingredient from the gel.

Preferably, the block ratio of the tri-block copolymer in said composition, which ratio is defined as the ratio between the sum of the number average molecular weight of the B-blocks and the number average molecular weight of the A-block ranges from 1.4 to 2.6.

By covalently binding the hydroxyl end-groups of the tri-block copolymer to a compound containing radiopaque atoms, many applications of said compositions become available:

For example, it may be visualized where a composition of the invention has been injected. This 3D in situ marking of a location may be useful, for example in radiotherapy for example breast or prostate cancer, where it is necessary to focus the energy beam at exactly the same location for sequential radiation exposures. Current positioning techniques include surgical introduction of small objects of gold, titanium or other electron dense objects that give sufficient contrast in x-ray and CT-imaging. However, these 'contrast agent markers or beckons are permanent and as such less attractive for the patient and may eventually cause scare tissue and bio-mechanic complications.

Also, in situ marking of a location may be useful when during surgery an area is marked, which needs a follow-up. For example, during endoscopic inspection of the colon and other externally accessible parts of the body, small surgical procedures may be performed either on the spot, or during a follow-up session, to burn or cut away tissue, such as small neoplasmas in the colon, which potentially could develop into tumours in the colon. Leaving behind a radiopaque gel depot will greatly facilitate revisiting of the site for inspection for follow-up procedures, thereby using image-guided techniques for positioning.

Treatment and subsequent inspection and follow-up of lesions in the gut, stomach or lung are done at shorter intervals, but again, the in situ marking of a location is desired.

Currently, to actually pin-point and revisit or inspect a previous site of treatment is not easy, as the form, shape and position, for example of the colon, may fold and twist and may alter the external positioning parameters.

Also, the temporary in situ marking of a location in vivo may be useful when successive injections need to be made at or next to previous injection sites. These radiopaque gels are far more compatible to the surrounding tissue than metal objects, and if desired, will erode away over time.

Furthermore, in the composition of the invention, the radiopaque atom stays with the gel since the atom forms part of the tri-block copolymer. This in contrast to other contrasting agents, which will readily diffuse away from the injection site.

As indicated before, the residence time of the composition of the invention can be anything in the range from some days to months.

Preferably, in said compositions, chemical hydrolysis or enzymatic cleavage at physiological conditions in situ of the tri-block copolymer wherein at least part of the hydroxyl end-groups of the tri-block copolymer is covalently bound to a compound containing one or more radiopaque atoms is limited, for example by choosing a suitable end-group linker and/or a suitable monomer, for example a hydrophobic monomer to link the compound containing one or more radiopaque atoms to.

Also, the composition of the invention comprising the tri-block copolymer wherein at least part of the hydroxyl end-groups of the tri-block copolymer is covalently bound to a compound containing one or more radiopaque atoms could be used to observe gel-erosion in vivo and to be able to correlate the gel-volume with degree of release of pharmaceutically active ingredient.

The tri-block copolymer wherein at least part of the hydroxyl end-groups of the tri-block copolymer is covalently bound to a compound containing one or more radiopaque atoms may be mixed blended with a tri-block copolymer that does not contain a compound containing one or more radiopaque atoms to fine tune for example i) the quantity, ii) the contrast intensity and iii) the duration of retention on the spot of injection.

In another aspect therefore, the invention relates to a method for imaging a position within the body of a warm-blooded species comprising the steps of:—injecting a composition comprising a tri-block copolymer accordingly to formula (1) B-A-B (1) wherein A stands for a linear poly-(ethylene glycol) block and wherein B stands for a poly (lactide-co-ε-caprolactone) block, wherein at least part of the hydroxyl end-groups of the tri-block copolymer are covalently bound to a compound containing a radiopaque atom of the invention into the body of the warm-blooded species and imaging the composition using conventional imaging methods such as CT or micro CT.

In the tri-block copolymer according to formula (1)

B-A-B (1)

A may stand for a linear hydrophilic block, for example for linear poly-(ethylene glycol) block (PEG block). Generally, the number average molecular weight (Mn) of the PEG block in the tri-block copolymer is at least 750 Da, for example at least 1000 Da, for example at least 1500 Da and/or preferably at most 5000 Da, for example at most 2000 Da. For example, the number average molecular weight of the PEG block ranges from 1000 to 5000 Da, preferably from 1000 to 2000 Da, for example from 1000 to 1500 Da. The number average molecular weight as used herein is defined as the number average molecular weight as determined using $^1$H nuclear magnetic resonance.

Poly-(ethylene glycol) is a diol also known as poly (ethylene oxide) and both names can be used interchangeably for the purpose of the invention.

In the tri-block copolymer according to formula (1)

B-A-B (1)

B may stand for a (linear) hydrophobic block, for example for a hydrophobic block containing ester and/or carbonate bonds.

B may for example stand for a hydrophobic block comprising at least one, preferably at least two cyclic monomers selected from the group consisting of glycolide, lactide, ε-caprolactone, p-dioxanone (1,4-dioxan-2-one), trimethylene carbonate (1,3-dioxan-2-one), 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, chi.-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one, β-propiolactone, γ-butyrolactone, δ-valerolactone, ε-decalactone, 3-methyl-1,4-dioxane-2,5-dione, 1,4-dioxane-2,5-dione, 2,5-diketomorpholine, α,α-diethylpropiolactone, 6,6-dimethyl-dioxepan-2-one, 6,8-dioxabicycloctane-7-one and 5,5-dimethyl-1,3-dioxan-2-one, wherein the hydroxyl end-groups of the tri-block copolymer in case they are acylated are acylated with an optionally substituted acyl having 2 to 12 C-atoms, C-atoms of the substituents included.

(Bio)degradation in the context of the present invention may be assessed in vitro by various analytical techniques including size-exclusion chromatography, nuclear magnetic resonance, MALDI-TOF, high pressure liquid chromatography or combinations of those.

The B-blocks may for example comprise monomer combinations comprising between 50 and 100 mol %, for example between 60 and 95 mol %, for example between 75 and 90 mol % glycolide.

The B-blocks may for example comprise monomer combinations comprising between 50 and 100 mol %, for example between 60 and 95 mol %, for example between 75 and 90 mol % ε-caprolactone.

The B-blocks may for example comprise monomer combinations comprising between 50 and 100 mol %, for example between 60 and 95 mol %, for example between 75 and 90 mol % lactide.

The B-blocks may for example comprise monomer combinations comprising between 50 and 100 mol %, for example between 60 and 95 mol %, for example between 75 and 90 mol % trimethylene carbonate.

Other combinations of the listed monomers are also possible, and the skilled person is able to choose them according to the polymer properties that they need for a specific application.

Preferably, the cyclic monomers of the B-blocks are selected from the group consisting of glycolide, lactide, ε-caprolactone, trimethylene carbonate and 1,3-dioxan-2-one, more preferably from the group consisting of lactide and ε-caprolactone. Preferred combinations of cyclic monomers in the B-blocks of the copolymers according to the present invention include but are not limited to:

glycolide and a monomer of the group of 1,3-dioxan-2-one, 5,5-dimethyl-1,3-dioxan-2-one, 1,4-dioxan-2-one, 1,4-dioxepan-2-one, 1,5-dioxepan-2-one.
  lactide and a monomer of the group of 1,3-dioxan-2-one, 5,5-dimethyl-1,3-dioxan-2-one, 1,4-dioxan-2-one, 1,4-dioxepan-2-one, 1,5-dioxepan-2-one.
  1,3-dioxan-2-one and a monomer of the group of 5,5-dimethyl-1,3-dioxan-2-one, 1,4-dioxan-2-one, 1,4-dioxepan-2-one, 1,5-dioxepan-2-one.
  ε-caprolactone and a monomer of the group of 1,3-dioxan-2-one, 5,5-dimethyl-1,3-dioxan-2-one, 1,4-dioxan-2-one, 1,4-dioxepan-2-one, 1,5-dioxepan-2-one.

Most preferably, B stands for a poly(lactide-co-ε-caprolactone) block (PLCA block), which PLCA block is a copolymer of lactide and ε-caprolactone. Within the framework of the invention the term lactide refers to all enantiomerically enriched, racemic forms and cyclic ester forms of lactic acid, such as L-lactide, D-lactide and DL-lactide.

The number average molecular weight of each individual B-block, preferably of the PLCA block as determined using $^1$H NMR as described herein is at least 400 Da, for example at least 450 Da, preferably at least 500 Da, and/or at most 1500 Da, for example at most 2000 Da, for example at most 2500 Da, preferably at most 3000 Da, for example at most 5000 Da. For example, the number average molecular weight of the PLCA block ranges from 400 to 3000, for example from 450 to 2000, for example from 500 to 1500 Da.

The block ratio of the tri-block copolymer is defined as the ratio between the sum of the number average molecular weight (Mn) of the B-blocks and the number average molecular weight (Mn) of the A-block, wherein the number average molecular weight of the A and of the B-blocks is determined using $^1$H NMR as described herein.

The block ratio of the tri-block copolymer(s) may range from at least 0.8, for example at least 1.0, for example at least 1.1, for example at least 1.2, for example at least 1.3, for example at least 1.4, for example at least 1.6, for example at least 1.8 to at most 5, for example at most 3, for example at most 2.6, for example at most 2.4, for example at most 2.2, for example at most 1.8, for example at most 1.4.

Preferably, the block ratio ranges of the at least two tri-block copolymers from 1.4 to 2.6, for example from 1.8 to 2.6, for example from 1.8 to 2.4.

The hydroxyl end-groups of the tri-block copolymer are at least partially acylated with an optionally substituted acyl having 2 to 12 C-atoms, C-atoms of the substituents included. The acyl group may be represented by a compound of formula (2)

$$R^1-C(O)- \qquad (2)$$

wherein $R^1$ stands for an optionally substituted alkyl, optionally substituted alkenyl, optionally substituted alkynyl or optionally substituted aryl, preferably for an optionally substituted alkyl or optionally substituted aryl, preferably an optionally substituted alkyl and wherein the $R^1$—C(O) group is covalently linked to the tri-block copolymer.

Examples of $R^1$ include but are not limited to linear and branched alkyls, for example methyl, ethyl, n-propyl, i-propyl, n-butyl, i-butyl, pentyl, hexyl, heptyl, octyl, nonyl, decyl and undecyl; linear and branched alkenyls; and linear and branched alkynyls. $R^1$ may also stand for the cyclic form of the alkyl, alkenyl or alkynyl. An example of optionally substituted aryl includes but is not limited to phenyl and halogen, for example iodine substituted phenyls.

Preferably, $R^1$ stands for an alkyl, preferably for methyl, ethyl. (in other words the acyl group is acetyl or propionyl).

$R^1$ may optionally be substituted with a functionalized group, for example with a group containing a heteroatom, for example O, N, for example an $NH_2$ group, S, for example an SH group, halogen, for example a fluoride, chloride or iodine group, preferably with iodine.

The hydroxyl end-groups of the tri-block copolymer may be acylated using methods known in the art, for example by reaction of the hydroxyl end-groups with an acid chloride or with an anhydride.

For example, acylation of the hydroxyl end-groups of the tri-block copolymer may be done using acetyl chloride (which is an unsubstituted acyl having 2 C-atoms), with propionyl chloride (which is an unsubstituted acyl having 3 C-atoms), etc.

For example, acylation of the hydroxyl end-groups of the tri-block copolymer may be done by reacting with the corresponding anhydride in pyridine at elevated temperature.

With 'degree of modification' is meant that the percentage of end-groups, preferably hydroxyl end-groups, that is modified. As used herein, 'degree of modification' is also referred—in case the end-groups are acylated as the 'degree of acylation'. The degree of modification may range from 0 and is at most 100%; for example the degree of modification (of one of the tri-block copolymers) of the hydroxyl end-groups is at least 25%, for example at least 30%, for example at least 35%, for example at least 40% and/or at most 95%, for example at most 90%, preferably 100%. For the avoidance of doubt, a degree of modification of 100% means that all hydroxyl end-groups of the tri-block copolymer have been modified; a degree of modification of 50% means that half of the hydroxyl end-groups have been modified and a degree of modification of 0% means that none of the hydroxyl end-groups have been modified. The degree of modification, is preferably calculated using $^1$H nuclear magnetic resonance by comparing integrals of the peaks due to the acylated hydroxyl end-groups and the integrals of the polyethylene glycol (as a measured for the amount of non-acylated hydroxyl end-groups).

In a preferred embodiment of the invention, one of the at least two tri-block copolymers has a degree of modification of 100% and one of the at least two tri-block copolymers has a degree of modification of 0%. This is preferred since a tri-block copolymer having a degree of modification of 0% is easily reproduced. A tri-block copolymer having a degree of modification of 100% can also be easily reproduced, for instance by using an excess of the compound with which the hydroxyl end-groups are acylated.

Preferably, the at least two types of B-A-B types of tri-block copolymers differ only on the degree of modification of the end-groups. By mixing the B-A-B type of tri-block copolymer having a degree of modification of 100% with a B-A-B type of tri-block copolymer having a degree of modification of 0% in different ratios, different compositions with a reproducible degree of total modification of the end-groups in the composition can be prepared. The reproducibility of the degree of modification of the end-groups in the composition is much higher than if this had to be achieved via synthesis of a single tri-block copolymer, hence a higher reproducibility and accuracy of the medication can be obtained.

Furthermore, by choosing the same (at least) two types of B-A-B tri-block copolymers, which differ only on the degree of modification of the end-groups, regulatory approval only needs to be obtained for these (at least) two types of B-A-B tri-block copolymers; whereas many different compositions having different final degrees of modification of end-groups in the composition can be prepared there from.

In the context of the invention, with 'degree of total modification of the end-groups in the composition' is meant the total amount of end-groups of all tri-block copolymers present that is modified. For example a final degree of modification of the end-groups in the composition of 100% means that all hydroxyl end-groups of the tri-block copolymers in the composition have been modified; a degree of total modification of the end-groups in the composition of 50% means that half of the hydroxyl end-groups of the tri-block copolymers in the composition have been modified.

Alternatively, one of the at least two tri-block copolymers have a degree of modification of 100%. This is another preferred embodiment, since a tri-block copolymers having a degree of modification of 100% can be easily reproduced, for instance by using an excess of the compound with which the hydroxyl end-groups are acylated.

Preferably, the at least two types of B-A-B types of tri-block copolymers differ only on the type of end-group. In a preferred embodiment of the invention, the composition comprises a mixture of a first B-A-B type of triblock copolymer having a specific end-group and a second B-A-B type of triblock copolymer which differs only from the first tri-block copolymer in its end-group.

Figure 1:
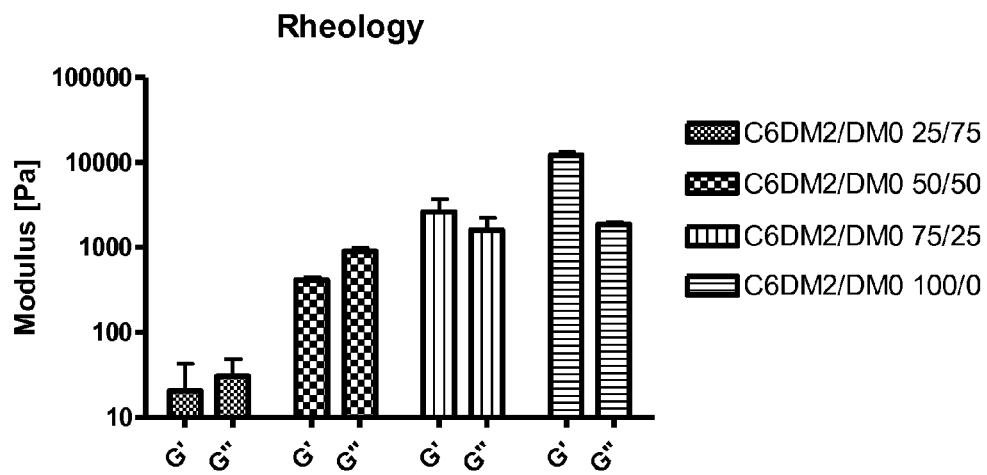
FIG. 1 shows the rheological properties at 37° C. of mixtures containing PLCA-PEG-PLCA and PLCA-PEG-PLCA hexanoate. Gels were 20% (w/w). Measurement frequency and strain were 1 Hz and 1%, respectively. Error bars represent standard deviation (n=3) In FIG. 1 the following abbreviations are used.

The synthesis of the tri-block copolymer as used in the composition of the invention can be done using methods known in the art, for example by ring-opening polymerization or polycondensation reactions. For example, the tri-block copolymer wherein the B block is a poly(lactide-co-ε-caprolactone) block (PLCA block) may be synthesized (analogous to) the method described by Seongbong, Jo et al. in 'Reverse thermal gelation of aliphatically modified biodegradable triblock copolymers', Macromol. Biosci. (2006), pages 923-928, which article is hereby included by reference. FIG. 1 as described herein gives the reaction scheme for the synthesis of a tri-block copolymer of PLCA-PEG-PLCA and its acylation of the hydroxyl end-groups with aliphatic acid chloride.

B blocks can be polymerized by using the cyclic monomers mentioned above in a ring-opening polymerization using the hydroxyl end-groups of poly(ethylene glycol) to initiate the polymerization. This is a very controlled and straightforward way of preparing triblocks in one step for people skilled in the art. Schemes and details for similar ring-opening polymerization reactions can be found in several patents or patent applications including and not limited to EP0863745 and WO0018821.

Preparing B blocks by polycondensation reactions using the open form of the cyclic monomers mentioned above, such as lactic acid, glycolic acid, epsilon-hydroxyhexanoic acid and the like is also possible, but less preferred since obtaining well-defined blocks in terms of average molecular weight and end-group functionality with polycondensation reactions is difficult.

Modification of the end-groups of the tri-block copolymer(s) in the composition of the invention may be done using methods known per se. For example, acylation of the hydroxyl end-groups may be done (analogous to) the method described in Seongbong, Jo et al. in 'Reverse thermal gelation of aliphatically modified biodegradable triblock copolymers', Macromol. Biosci. (2006), pages 923-928, and as illustrated by FIG. 1 therein, which article is hereby included by reference.

The number average molecular weight (Mn) of the tri-block copolymer depends on the number average molecular weight of the B and A blocks used, preferably respectively PLCA and PEG blocks. The number average molecular weight of the tri-block copolymer may be calculated using $^1$H nuclear magnetic resonance. Preferably the Mn of the tri-block copolymer ranges from 3,000 to 5,000 Da.

The weight ratio of ε-caprolactone to lactide is the weight of ε-caprolactone divided by the weight of lactide used to prepare the B-block with, in case the B-block is PLCA.

The weight ratio of ε-caprolactone to lactide is preferably at least 1/1, for example from 9/1 to 1/9, for example from 4/1 to 1/4, for example from 1/1 to 1/0, for example from 1/1 to 9/1.

For the avoidance of doubt, with weight ratio of ε-caprolactone to lactide is 1/0 is meant that only I only ε-caprolactone is present and no lactide. With weight ratio of ε-caprolactone to lactide is 0/1 is meant that only lactide is present and no ε-caprolactone.

The active ingredient in the composition of the present invention may be an active ingredient such as any pharmaceutically active ingredient and any diagnostic and any contrast agent and includes those pharmaceutically active ingredients having a prophylactic effect on the animal, including human as well as those pharmaceutically active ingredients that have an effect of alleviating, reducing or even completely eliminating a symptom, or a cause, or a consequence of a disease, such as pain, swelling or inflammation or a disease from the animal, including human. For example, the pharmaceutically active ingredient may include broad classes of compounds normally delivered into the body. For example, these pharmaceutically active ingredients include but are not limited to anti-infectives (including antibiotics, antivirals, fungicides, scabicides or pediculicides); antiseptics (e.g. benzalkonium chloride, benzethonium chloride, chorhexidine gluconate, mafenide acetate, methylbenzethonium chloride, nitrofurazone, nitromersol and the like); analgesics and analgesic combinations; anorexics; antihelminthics, antiarthritics, antiasthmatic agents; anticonvulsants; antidepressants; antidiabetic agents; antidiarrheals; antihistamines; anti-inflammatory agents, antimigraine preparations; antinauseants; antineoplastics; antiparkinsonism drugs; antipuritics; antipsychotics; antipyretics, antispasmodics; anticholinergics; sympathomimetics; xanthine derivatives; cardiovascular preparations including potassium and calcium channel blockers; beta-blockers; alpha-blockers and antiarrhythmics; antihypertensives; diuretics and antidiuretics; vasodilators including general coronary, peripheral and cerebral vasodilators; central nervous system stimulants; vasoconstrictors; cough and cold preparations, including decongestants; hormones and steroids (e.g. estrogens, progestins, androgens, adrenocorticoids, corticosteroids and the like); hypnotics; immunosuppressives; muscle relaxants; parasympatholytics; psychostimulants; sedatives and tranquilizers, narcotics (e.g. morphine, meperidine, codeine and the like), local anesthetics (e.g. amide- or anilide-type local anesthetics such as bupivacaine, dibucaine, mepivacaine, procaine, lidocaine, tetracaine and the like); antiemetic agents (e.g. ondansetron, granisetron, tropisetron, metoclopramide, domperidone, scopolamide and the like); antiangiogenic agents (e.g. combrestatine, contortrostatin, anti-VEGF and the like), polysaccharides, immune-modulating, anti-thrombogenic compounds, anti-claudicating drugs, anti-atherosclerotic drugs, antihistamines, anti-cancer drugs (e.g. mechlorethamine, cyclophosphamide, fluorouracil, thioguanine, carmustine, lomustine, melphalan, chloambucil, streptozocin, methotrexate, vincristine, bleomycin, vinblastine, vindesine, dactinomycine, daunorubicin, doxorubicin, tamoxifen, paclitaxel, epirubicin, mitomicin C, cisplatin, carboplatin, and the like and photosensitizers used in photodynamic therapy, vascular drugs, ophthalmic drugs, amino acids, vitamins, neurotransmitters, neurohormones, signaling molecules, psychoactive medicaments, synthetic drugs, semi-synthetic drugs, natural drugs and substances derived from these, or combinations of the above.

The pharmaceutically active ingredient may also be a biological including but not limited to (recombinant) proteins, PEGylated-proteins and peptides (e.g. insulin, erythropoietin, exenatide, glucagon-like-peptide-1, morphogenic proteins (e.g. bone morphogenic proteins, transforming growth factors, fibroblast growth factors, tumor necrosis factors), receptor antagonists (e.g. Interleukin-1-receptor-antagonist), anticancer proteins (e.g. neocarzinostatin, L-asparaginase, interleukin-2, bevacizumab and other anti-VEGF agents) prophylactic vaccines, therapeutic vaccines, genetic materials (e.g. nucleic acid sequences, polynucleotides, (antisense) oligonucleotides, plasmids, DNA, RNA, siRNA, microRNA), aptamers, enzymes, antigens, antibodies, antibody fragments, viruses, virus-based materials, cells, cellular substructures, etc.), Prodrugs, metabolites, derivatives, in-vivo or in in-vitro chemically modified products, in-vivo or in-vitro enzymatic modified products and pharmaceutically active degradation products of the pharmaceutical active ingredients described herein are included in the scope of the invention.

Preferably, the active ingredient is a pharmaceutically active ingredient chosen from the group of immune-modifying drugs, anti-inflammatory drugs or growth factors.

Preferably, the active ingredient is a pharmaceutically active ingredient chosen from the group of immune-modifying drugs for example cyclosporine, tacrolimus (FK-506), sirolimus or rapamycin.

Preferably, the active ingredient is a pharmaceutically active ingredient chosen from the group of steroidal anti-inflammatory drugs, for example prednisone, prednisolon, triamcinolon, clobetasol or betamethason.

Preferably, the active ingredient is a pharmaceutically active ingredient chosen from the group of non-steroidal anti-inflammatory drugs, for example aspirin, diclofenac, piroxicam, meloxicam, ibuprofen or a selective COX-2 inhibitor for example celecoxib, valdecoxib, etoricoxib or rofecoxib.

Preferably, the active ingredient is a pharmaceutically active ingredient chosen from the group of anticancer agents for example bevacizumab, tamoxifen or interleukin-2.

Preferably, the active ingredient is a pharmaceutically active ingredient chosen from the group of anti-viral agents for example acyclovir or oseltamivir.

Preferably, the active ingredient is a pharmaceutically active ingredient chosen from the group of anti-bacterial agents for example amoxicillin.

Preferably, the active ingredient belongs to the class of human growth hormones and its biosimilar derivatives, which can be applied in both pediatric and adult growth disorders, maintaining sufficient musculature, and for anti-ageing applications.

Preferably, the active ingredient is a pharmaceutically active ingredient effective against inflammation or microbial infections of the inner ear and its connecting tissues, (intra-tympanic ear diseases).

Preferably, the active ingredient is a pharmaceutically active ingredient effective against forms of diabetes, for example glucagon-like-peptide-1, and its derivatives such as exendin-4 and liraglutide.

Preferably, the active ingredient is a pharmaceutically active ingredient chosen from the group of vaccines.

Preferably, the active ingredient is a pharmaceutically active ingredient chosen from the group of ophthalmic agents for example Triamcinolone and Bevacizumab.

Preferably, the active ingredient is a pharmaceutically active ingredient effective against forms of neuro-degenerative diseases such as apomorphine, rivastigmine, pramipexole, pioglitazone, memantine and safinamide.

Preferably, the active ingredient is a pharmaceutically active ingredient chosen from the group of biologicals including but not limited to growth factors which are very suitable for application in orthopedics and in particular in the prevention or treatment of diseases of intervertebral discs, or cartilage, or bone. Examples of such growth factors include but are not limited to transforming growth factor 3, fibroblast growth factor 18, osteogenic protein 1, bone morphogenic protein 2, bone morphogenic protein 6, bone morphogenic protein 7, interleukin-1-receptor-antagonist.

Preferably, the active ingredient is a pharmaceutically active ingredient effective against forms of diabetes, for example glucagon-like-peptide-1, exenatide, amylin.

The pharmaceutically active ingredient may for example be an agent to suppress or slow down cancerous growth or neovascularisation, such as anti-VEGF agents, si-RNA or aptamers or antistatics, such as rapamycin.

Examples of anticancer agents include doxorubicin, daunorubicin, epirubicin, mitomicin C, paclitaxel, cis-platin, carboplatin, and anticancer proteins such as neocarzinostatin, L-asparaginase, and the like and photosensitizers used in photodynamic therapy.

The pharmaceutically active ingredient may for example be an agent to avoid, control, suppress, or eradicate infectious diseases.

Preferably, the active ingredient is a pharmaceutically active ingredient chosen from the group of non-steroidal anti-inflammatory drugs, for example a steroid or a selective COX-2 inhibitor; and biologicals, for example a (monoclonal) antibody, protein, peptide or cell extract.

The solvent in the composition of the present invention is preferably a solvent that is non toxic, preferably also biocompatible, and approved by regulatory instances, preferably aqueous based or a so-called FDA (Federal Drug Administration) class 3 solvent.

Examples of solvents include but are not limited to water, mixtures of water and an organic solvent like for example ethanol, isopropanol or dimethylsulfoxide (DMSO); aqueous buffer solutions, preferably aqueous buffer solutions that lead to isotonic compositions of the invention, such as PBS (phosphate buffered saline) or Sorenson modified buffer or variants thereof; and organic solvents, such as ethylacetate, acetone, dichloromethane (DCM), dimethylsulfoxide (DMSO), N-methylpyrrolidone (NMP), isopropyl myristate and benzyl benzoate.

With 'isotonic' is meant that the solution a solution having an osmotic pressure comparable to or at least compatible with the osmotic pressure of human or animal bodily fluids, preferably with blood.

Preferably the solvent is water or an aqueous buffer solution, more preferably an aqueous buffer solution that leads to an isotonic composition of the invention.

The pH of the solvent is preferably in the range from 5 to 8, for example in the range from 6.5 to 7.5. More preferably, the pH of the solvent is chosen such that the pH of the composition of the invention is about neutral (in the range from 5 to 8, preferably in the range from 6.5 to 7.5).

With gel temperature is meant the temperature at which the tri-block copolymer in the solvent chosen forms a gel. Vial tilting as described below can be used to determine the gel temperature.

The gel temperature of the composition of the invention is preferably at least 20° C., more preferably at least 25° C., for example at least 30° C. and/or preferably at most 36, for example at most 35, for example at most 34° C. For example, the gel temperature of the composition of the invention ranges from 30 to 35° C.

With phase separation temperature is meant the temperature at which the different components present are not capable of forming a homogeneous solution, but instead form separate (liquid) phases. Phase separation can be determined using vial tilting. To this end, the compositions of the invention are vortexed and stored at 5° C. If needed, the samples were subjected to another heating and cooling cycle until all components in the composition of the invention were completely dissolved. The samples were evaluated by vial tilting at 5° C., then allowed to equilibrated at 20° C. for 30 minutes after which they were evaluated again. Visual observations were made and noted down. Next, the samples were placed in a water bath and slowly heated (less than 0.5° C./min). At every 1° C. increment, samples were evaluated by vial tilting and considered a gel if no flow was observed during a period of 15 seconds. Samples were heated until phase separation was observed and the temperature at which phase separation was observed is the 'phase separation temperature'. Preferably, the phase separation temperature of the composition of the invention is at least 25° C., for example at least 30° C., for example at least 40° C., for example at least 41° C., for example at least 42° C.

Preferably, for clinical applicability, the tri-block copolymer has a gel window between 30° C. and 50° C., for example between 30° C. and 42° C. With 'gel window' is meant the 'window between the gel temperature and the phase separation temperature', in other words it is the entire temperature range in which the tri-block copolymer is a gel.

The concentration of tri-block copolymers in the composition of the invention is in principle not critical, but will generally be from 10 to 40% w/w, preferably from 15 to 35% w/w, for example from 20 to 35% w/w based on the amount of solvent and active ingredient present in the composition.

The ratio in which the tri-block copolymers in the composition of the invention are mixed to obtain the desired release profile of the active ingredient can easily be determined by the skilled person. For example, the weight ratio of the at least two types of tri-block copolymers may range from 0.1/99.9 to 99.9/0.1, for example from 25/75 to 50/50 or from 75/25 to 50/50. Preferably the weight ratio of the at least two types of tri-block copolymers is at least 75/25.

The amount of active ingredient in the composition of the present invention depends on the amount to be administered to the animal, including human and on the duration of the release. For example, the amount of active ingredient may be up to and including 50% w/w based on the tri-block copolymers in the composition if a high loading of the drug is desired, but may also for example be less, for example an amount of up to and including 40, for example up to and including 30, for example up to and including 20% w/w based on the triblock copolymers in the composition and/or for example at least 0.01% w/w, preferably at least 0.1% w/w, for example at least 1% w/w based on the triblock copolymers in the composition.

The invention also relates to a composition of the invention, wherein the composition is a pharmaceutical composition further comprising a pharmaceutically acceptable adjuvant, carrier, excipient, contrast agent or dye.

The invention also relates to a composition, wherein the composition further comprises nano-particles and/or microparticles (such as liposomes and microspheres) which themselves contain the pharmaceutically active ingredients as described above.

A person skilled in the art knows which carriers can be used as pharmaceutically acceptable carriers. Examples of such pharmaceutically acceptable carriers are both inorganic and organic carrier materials, suitable for oral/parenteral/injectable administration and include water, polyethyleneglycol (PEG), polypropyleneglycol (PPG), cellulose derivatives, such as hydroxypropylmethylcellulose (HPMC), hydroxyethylmethylcellulose (HEMC), hydroxyethylcellulose (HEC); polyvinylpyrrolidone (PVP), polyvinylalcohol (PVA), gelatin, gum arabic, lactose, starch, magnesium stearate, talc, vegetable oils, and the like.

Also, the person skilled in the art knows which pharmaceutically acceptable adjuvants and excipients may be used in the compositions of the invention. Examples of conventional pharmaceutical additives and adjuvants, excipients or diluents, including, but not limited to, water, gelatin of any origin, polyethyleneglycol (PEG), polypropyleneglycol (PPG); cellulose derivatives, such as hydroxypropylmethylcellulose (HPMC), hydroxyethylmethylcellulose (HEMC) or hydroxyethylcellulose (HEC); polyvinylpyrrolidone (PVP), polyvinylalcohol (PVA), vegetable gums, ligninsulfonate, talc, sugars, starch, gum Arabic, vegetable oils, polyalkylene glycols, flavoring agents, preservatives, stabilizers, emulsifying agents, buffers, lubricants, colorants, wetting agents, fillers, imaging agents, such as contrast agents for X-ray or MRI; and the like, for example iodo compounds, such as the commercially available Xenetic® and Hexabrix®.

In another aspect, the invention relates to a composition according to the invention for use as a medicament.

In another aspect, the invention relates to a composition according to the invention for use as a medicament that is injected through a needle of at least 18 G, for example at least 21 G, preferably at least 23 G, for example at least 27 G, for example at least 30 G.

With G is meant 'Gauge' which is a measure for the outer diameter of a needle. Smaller gauge numbers indicate larger outer diameters and as such 'larger needles'. For ease of injection, smaller needles are preferred to larger needles. Inner diameters of a needle depend on both gauge and wall thickness.

The invention can also contain and release micro- or nano-sized particles such as microspheres and liposomes which already contain for instance drugs, nucleotide sequences or imaging agents.

The benefit of combining the invention with these micro- or nano-sized particles is that the invention will ensure localization and gradual release of these particles, instead of a typical migration of such particles from the place of injection.

Examples of contrast agents include iodo compounds. Exemplary iodo compounds are commercially available as Xenetic® and Hexabrix®.

Depending on the pharmaceutically active ingredient or combination of pharmaceutically ingredients present in the composition of the invention, different diseases may be targeted, preferably treated using the composition(s) of the present invention.

In another aspect, the invention relates to a method for preparing a composition according to the invention suitable for forming a thermogel comprising the step of mixing at least two types of B-A-B types of tri-block copolymers of formula (1)

$$B-A-B \qquad (1)$$

wherein B stands for a hydrophobic block and wherein A stands for a hydrophilic block wherein the at least two types of B-A-B types of tri-block copolymers differ only on the type of end-group and/or on the degree of modification of the end-groups.

The was the polymer mixture is prepared is in principle not critical; it is for example possible to dissolve each polymer separately in the solvent of choice or for example it is possible and preferred to dissolve the polymers in a solvent, which solvent is thereafter evaporated. The dried polymer mixture can then be dissolved in the solvent of choice.

In yet another aspect, the invention relates to a process for the preparation of a composition of the invention comprising the steps of synthesizing the tri-block copolymer and mixing the tri-block copolymer with the active ingredient and the solvent. The order in which the tri-block copolymers and the active ingredient are dissolved in the solvent is in principle not critical; it is for example possible to first dissolve the tri-block copolymers and then the active ingredient, to first dissolve the active ingredient and then the tri-block copolymers or for example to dissolve both the active ingredient and the tri-block copolymers at the same time in the solvent of choice. However, for active ingredients that are highly soluble in the solvent, preferably first the active ingredient is dissolved in the solvent to form a solution of the active ingredient in the solvent, after which the tri-block copolymers are dissolved into said solution. For active ingredients that are less soluble in the solvent of choice, the active ingredient may first be dissolved into a solvent in which it is better soluble (for example a hydrophobic drug may be soluble in ethylacetate), after which the polymers are added and dissolved, after which the solvent is evaporated and the solvent of choice is added to the (dried polymer) mixture. This will increase the solubility of the active ingredient in the solvent of choice.

To facilitate dissolving the tri-block copolymer and/or the active ingredient, the composition comprising the tri-block copolymer, the solvent and the active ingredient may be heated for example until the tri-block polymer melts. For example, the heating of the composition may be performed at 50° C.

Preferably, if the active ingredient is sensitive to heat, the tri-block copolymer may be melted (for example at a temperature of about 50° C.), dissolved into the solvent of choice after which the obtained solution may be cooled down and the active ingredient may be dissolved in the solvent.

In another aspect, the invention relates to a method for delivering an pharmaceutically active ingredient over an extended period, for example over a period of more than 1 day up to several, e.g. 6, months, to an animal, including a human requiring such treatment which comprises administering to such animal an effective amount of the composition of the invention. In yet another aspect, the invention relates to a method for delivering an pharmaceutically active ingredient over an extended period, for example over a period of more than 1 day up to several, e.g. 6, months, to an animal, including a human requiring such treatment which comprises administering to such animal an effective amount of the composition of the invention through a needle of at least 18 G, for example at least 21 G, preferably at least 23 G, for example at least 27 G, for example at least 30 G. In the framework of the invention, with animals is meant all animals, including mammals, examples of which include humans. Preferred examples of mammals beside humans include but are not limited to dogs, cats, dromedaris, camels, elephants, lama's, goats, mice, guinea pigs, rabbits, pigs, cows, water buffalos, kangaroos, monkeys and horses.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention is now elucidated by way of the following examples, without however being limited thereto.

EXAMPLES

Measurement Methods

The triblock copolymer composition (PLCA/PEG ratio, cap/lac ratio and DM) was analyzed with proton nuclear magnetic resonance ($^1$H NMR; Varian, 400 MHz), using deuterated chloroform as solvent and reference. From the integration of various proton signals (due to PEG and incorporated monomers), absolute number average molecular weights $M_n$ were obtained. Mn of the tri-block copolymer is the sum of the molecular weights of the central PEG block and the two polyester blocks (ratio of blocks determined with NMR).

The block ratio as used herein is the weight ratio of the PLCA-blocks to the PEG-block (of known molecular weight) and can be calculated from grams of monomers (lactide+caprolactone) divided by grams of PEG used to synthesize the tri-block copolymer. Final triblock composition after polymer purification was checked with $^1$H NMR by comparing integrals of peaks due to PEG and incorporated ring-opened monomers. The weight ratio of ε-caprolactone to L-lactide can be calculated from NMR by comparing integrals of peaks due to ring-opened lactide and caprolactone The integrals of peaks due to acyl endgroup and PEG block were used to calculate the degree of modification (DM range 0-2, which corresponds to a degree of acylation of 0 to 100%).

Example 1 Synthesis of (Unmodified) PLCA-PEG-PLCA

In a three-neck round-bottom flask with a Dean Stark trap and condenser on top, 12.5 g PEG 1500 (8.3 mmol) and 125 ml toluene were stirred and heated at 150° C. under a nitrogen atmosphere. PEG was dried azeotropically by distilling off ca. 60 ml toluene/water.

After cooling down the solution to ca. 80-100° C., 3 g L-lactide (21 mmol) and 12 g caprolactone (105 mmol) were added. The solution was heated again at 150° C. and an additional 40 ml toluene/water was distilled off. The solution was then cooled down to ca. 80-100° C. and 0.2 ml stannous octoate was added. Ring-opening polymerization was carried out at 120° C. overnight under nitrogen atmosphere. The next day the solution was cooled down and the polymer was precipitated by addition of a 1:1 mixture of hexane and ether. At −20° C. the polymer solidified and non-solvents were decanted. The polymer was dried in vacuo. Yield: ca. 26 g soft wax.

Unmodified PLCA-PEG-PLCA, having a PLCA/PEG block ratio around 1.2 and a caprolactone/lactide weight ratio 4/1 was obtained. This tri-block copolymer is water-soluble; but does not form a thermogel at 37° C.

Example 2: Synthesis of Fully C6-Modified PLCA-PEG-PLCA

Polyethyleneglycol (PEG 1500, 15.5 g, 10.3 mmol) and ca. 135 ml toluene were charged into a 250 ml three-neck round-bottom flask equipped with a magnetic stirring bar. Using a Dean-Stark device with a condenser on top, 50 ml of toluene was distilled off to remove water (from PEG) azeotropically by heating at 150° C. at atmospheric pressure under nitrogen.

After cooling down the solution to ca. 80-100° C., L-lactide (3.7 g, 26 mmol) and caprolactone (15 g, 131 mmol) were added. 55 ml of toluene was distilled off to dry the monomers by heating at 150° C. at atmospheric pressure. Ca. 30 ml of dry toluene was left in the flask for the polymerization.

After cooling down the mixture to ca. 80-100° C., tin(II) 2-ethylhexanoate (0.25 ml) was added through one of the necks.

Polymerization was carried out at 120° C. for 1 day under nitrogen atmosphere.

After cooling down to room temperature, ca. 70 ml dichloromethane and 7 ml triethylamine (50 mmol) were added. Subsequently, 5.8 ml hexanoyl chloride (42 mmol) was added slowly to the stirred solution, which was cooled with an ice bath. The acylation reaction was continued for a few hours after which dichloromethane was removed by rotavap, and ethyl acetate (ca. 100 ml) was added to the residue. Triethylamine salt was removed by (paper) filtration and the polymer, which was dissolved in the clear filtrate was precipitated by addition of a (1:1) mixture of hexane and diethyl ether. At ca. −20° C. (in freezer) the polymer product separated as a waxy solid from which non-solvents could be decanted easily. Finally, the precipitated polymer was dried in vacuo. Yield: ca. 28 g.

The PLCA/PEG block ratio is around 1.2; caprolactone/lactide weight ratio 4/1. Degree of modification (from NMR) is ca. 2.

Example 3 Synthesis of Partially C6-Modified PLCA-PEG-PLCA with a (DM) Degree of Endgroup Modification of 1.5

Polyethyleneglycol (PEG 1500, 19.5 g, 13 mmol) and ca. 160 ml toluene were charged into a 500 ml three-neck round-bottom flask equipped with a magnetic stirring bar. Using a Dean-Stark device with a condenser on top, 60 ml of toluene was distilled off to remove water (from PEG) azeotropically by heating at 150° C. at atmospheric pressure under nitrogen.

After cooling down the solution to ca. 80-100° C., L-lactide (4.8 g, 33 mmol) and caprolactone (18.7 g, 164 mmol) were added. 60 ml of toluene was distilled off to dry the monomers by heating at 150° C. at atmospheric pressure. Ca. 40 ml of dry toluene was left in the flask for the polymerization.

After cooling down the mixture to ca. 80-100° C., tin(II) 2-ethylhexanoate (0.3 ml) was added through one of the necks.

Polymerization was carried out at 120° C. for 1 day under nitrogen atmosphere.

After cooling down to room temperature, ca. 50 ml dichloromethane and 4.2 ml triethylamine (32 mmol) were added. Subsequently, ca. 3.4 ml hexanoyl chloride (25 mmol) was added slowly to the stirred solution, which was cooled with an ice bath. The acylation reaction was continued for a few hours after which dichloromethane was removed by rotavap, and ethyl acetate (ca. 80 ml) was added to the residue. Triethylamine salt was removed by (paper) filtration and the polymer, which was dissolved in the clear filtrate was precipitated by addition of a (1:1) mixture of hexane and diethyl ether. At ca. −20° C. (in freezer) the polymer product separated as a waxy solid from which non-solvents could be decanted easily. Finally, the precipitated polymer was dried in vacuo. Yield: ca. 38 g.

The PCLA/PEG block ratio is around 1.2; caprolactone/lactide weight ratio 4/1. Degree of modification (from NMR) is ca. 1.5.

Example 4 Synthesis of Fully C12-Modified PLCA-PEG-PLCA

C12-modified PLCA-PEG-PLCA was made in the same way as the analogous C6-modified triblock described in example 2. In that case lauroyl chloride was used. Fully C12-modified PLCA-PEG-PLCA is insoluble in (cold) water (temperature of 7° C.).

Table 1 summarizes the results of the polymer synthesis and aliphatic modification. The molecular weights of the synthesized polymers were determined by NMR. The NMR spectra of PLCA-PEG-PLCA show characteristic peaks of lactide, caprolactone, and PEG at 5.1, 2.3, and 3.6 ppm, respectively.

TABLE 1

Characterization results of PLCA-PEG-PLCA and aliphatically modified PLCA-PEG-PLCA by NMR

| Polymer | PLCA/PEG (block ratio) | (weight ratio of ϵ-caprolactone to lactide) | Deegree of Modification (DM or degree of acylation) |
|---|---|---|---|
| PLCA-PEG-PLCA (I) | 1.2 | 4/1 | 0 (0%) |
| Partial C6-modified PLCA-PEG-PLCA (IV) | 1.2 | 4/1 | 1.5 (75%) |
| Fully C6-modified PLCA-PEG-PLCA (II) | 1.2 | 4/1 | 2 (100%) |
| Fully C12- modified PLCA-PEG-PLCA (III) | 1.2 | 4/1 | 2 (100%) |

PLCA/PEG: the ratio of PLCA to PEG

Example 5 Blending Fully Modified and Unmodified PLCA-PEG-PLCA

This example illustrates a method for making tri-block copolymer mixtures with various selectable reverse thermal gelation temperatures by mixing two pre-made individual tri-block copolymers. Tri-block copolymers prepared by the method described in Example 1 and 2 (PLCA-PEG-PLCA (I) and C6-modified PLCA-PEG-PLCA (II)) and Example 3 (C12-modified PLCA-PEG-PLCA (III)) were dissolved in Ethylacetate to form 500 mg/ml solutions. Two solutions of Component I and component II or III were mixed together. The mixture was placed in a petri dish under nitrogen flow overnight to evaporate ethyl acetate. The dried polymer mixture was dissolved in PBS, pH 7.4 to prepare different solutions.

Table 2 below summarizes blend compositions of fully modified (C6/C12) and unmodified PLCA-PEG-PLCA and their thermogelation behaviour in aqueous solution at 37° C. Note that most blends in aqueous solutions phase separate at 37° C.

TABLE 2

| Unmodified (wt %) | C6-modified (wt %) | C12-modified (wt %) | 20% solution in PBS at 37° C. | Phase separation at 37° C.: NA = not applicable |
|---|---|---|---|---|
| 100 | | | No thermogelling properties | NA |
| 75 | 25 | | No gel | No |
| 50 | 50 | | No gel | Yes |
| 25 | 75 | | Gel | Yes |
| 0 | 100 | | Gel | Yes |
| 0 | | 100 | Insoluble | NA |
| 25 | | 75 | No gel | No |
| 50 | | 50 | Gel | Yes |
| 75 | | 25 | Gel | Yes |

Example 6 Mechanical Properties

This example illustrates the measurement of the storage and loss modulus of mixture of tri-block copolymers.

The blends from Table 2 that form gels were tested.

Rheological characterization of the blends was done with a AR-G2 rheometer (TA Instruments, Etten-Leur, The netherlands) equipped with a 1° steel cone geometry of 20 mm diameter and solvent trap. Polymer blend solutions of 20% (w/w) were prepared in PBS pH 7.4 at 4° C. 300 µl of the solutions were placed in glass vial (8.2×40 mm) and incubated for around 3 hours at 37° C. to enable gelation and stabilization. Using a spatula, approximately 70 mg of the sample was placed between the pre-heated (37° C.) plates of the rheometer. Rheological gel characteristics were monitored by oscillatory time sweep experiments. During time sweep experiments G' (shear storage modulus) and G" (loss modulus) were measured for a period of 5 min. Also temperature sweep experiments were performed on the polymer solutions. Therefore the plates of the rheometer were pre-cooled at 4° C. Temperature increase was 1° C./min. When G"/G' (=tan δ)<1, the sample is considered as a gel in a rheological point of view. All experiments were performed at constant strain (1%) and frequency (1 Hz).

Example 7 Drug Release and Degradation in PBS+0.2% Tween 80

This example illustrates the drug release profile from tri-block copolymer mixture solutions of the present invention using celecoxib as a model drug of small hydrophobic molecule.

A polymer mixture was prepared as described in Example 5 except that a solution of celecoxib (CLB) in ethyl acetate was used. To the dried mixture of polymer and celecoxib PBS was added to obtain a final concentration of 20% (w/w) polymer based on the amount of celecoxib and PBS and 0.5 w/w % celecoxib on polymer. As described in Example 6, the polymer-celecoxib solutions were transferred with a syringe to a glass vial (8.2×40 mm). The vials were placed at 37° C. to allow gel formation. After 30 min 800 µl of PBS (+0.2% tween 80) was added. In this experiment Tween 80 was used in order to increase celecoxib solubility to around 100-200 ug/ml. This was necessary to faciliate sink conditions.

At predetermined time points, the buffer was removed and kept for celecoxib quantification, the weight of the remaining gel was measured and fresh buffer was added.

For comparison the same experiment was performed with the partially C6-modified PLCA-PEG-PLCA (DM 1.5).

Celecoxib concentration in the buffer was measured by a Waters Acquity™ Ultra Performance LC system (UPLC, Waters, Milford Mass., USA) equipped with an Acquity™ BEH C18 1.7 µm column (2.1×100 mm), a binary solvent manager, a sample manager with column oven at 50° C. and an Acquity™ TUV Detector (detection wavelength: 254 nm). After injection of 7.5 µl release sample, a gradient was run from 100% A (H2O/ACN 95/5% (v/v) containing 0.1% TFA) to 100% B (MeOH/ACN/H2O 45/45/10% (v/v) containing 0.1% TFA) in 2 minutes and kept at 100% B from 10 min at a flow rate of 0.08 ml/min. The run time was 16 min. A calibration curve was obtained after injection of standard celecoxib solutions in DMSO (0.5-100 ug/ml). The chromatograms were analysed using Empower Software Version 1154 (Waters, Milford Mass., USA). CLB concentration in the release sample was in the range 5-20 µg/ml.

The results of this example are shown in FIGS. 1 to 5.

Example 9 Synthesis of Non Acylated PLGA-PEG-PLGA (DM 0) and Acylated PLGA-PEG-PLGA (DM 2)

To a flask under a nitrogen atmosphere where added 20 g PEG 1500 (13.3 mmol), 13.5 g D-lactide (93.7 mmol), 13.5 g L-lactide (93.7 mmol), 13.5 g glycolide (116 mmol) and 200 mL toluene. 80 mL was distilled off azeotropically using Dean Stark apparatus. After cooling down to room temperature 0.4 g stannous octoate was added and the solution heated under refluxing conditions for 1 day. The resultant polymerization solution was equally divided into batch 1 and batch 2.

Batch 1 was cooled down to room temperature and precipitated in an excess of pentane and ether. The precipitated white product was dried under vacuum to give a solid.

Batch 2 was placed in a flask under a nitrogen atmosphere together with 40 mL dichloromethane, 7 mL triethylamine and the solutions was cooled with an ice-bath. 2 mL acetyl chloride was slowly added to this cold solution. After stirring for 3-4 hours the dichloromethane was removed in vacuo and 80 mL ethyl acetate was added. After filtering off the salts, the product was obtained by precipitation in a pentane/ether mixture. The yellowish polymer was dried under vacuum. The product was characterized by 1H-NMR to confirm the triblock copolymer was fully acylated (DM 2).

Experiment 10 Synthesis of Monoacetylated PLGA-PEG-PLGA (DM 1)

10 g of PLGA1500-PEG1500-PLGA1500 (2 mmol; 4 mmol OH) as synthesized in Example 9) was dissolved in 100 mL toluene and dried azeotropically, 80 mL was removed. The reaction was cooled down to room temperature and 10 mL dry dichloromethane, 0.6 mL triethylamine. The reaction was then further cooled using an ice bath and 0.25 mL acetyl chloride 3 mmol) was slowly added allowed to react for 1 day. The work-up was conducted as per experiment 9. A white waxy solid product was obtained.

Characterization by 1H-NMR showed that the degree of end-group modification (acetylation) was approximately 1.

Experiment 11 Rheological Characterization of PLGA-PEG-PLGA Compositions of the Invention The conditions for the rheology measurements were used as per Example 6. Plotting the storage modulus versus temperature for DM0, DM1, DM2 and DM0+DM2 shows that compositions DM1 and DM0+DM2 are both gels at 37° C. whereas DM0 and DM2 reach a gel state at either higher or lower temperature respectively. Next to this significant shift in the temperature of gelation, we also observe a significant difference in G' between DM=1 (430 Pa) and mix of DM=2/DM=0 50-50 (300 PA). The result is shown in FIG. 6.

Example 12 Chromatographic Method

By mixing polymers in this invention of the same block copolymer composition but with either only hydroxyl-end groups, or only aliphatic end-groups, and at different ratio's, one can generate an average Degree of Modification (DM) of 0.1 to 1.9, in order to fine tune the drug release and other characteristics of the formulation of the invention.

A method to distinguish between a composition comprising a mixture of DM0 and DM2 and a composition comprising also DM1 tri-block copolymer is hydrophilic interaction chromatography (HILIC).

Abrar and Trathnigg (Anal. Bioanal. Chem., 2001, 400, 2531-2537) describe a method for separating polyoxyethylenes according to the number of hydroxyl groups. In the compositions according to the invention, acylated tri-block copolymer compositions have fewer available hydroxyl groups than non-acylated compositions and thus it is expected that the method of Abrar and Trathnigg is suitable for distinguishing compositions of this invention comprising mixtures of tri-block copolymer compositions from compositions comprising a single and partially acylated tri-block copolymer.

Separation in HILIC is achieved by partitioning the composition between the aqueous layer surrounding the stationary phase and the mobile organic phase. Samples with a higher organic content (acylated) will elute before non-acylated compositions as shown in FIGS. 7 and 8.

FIG. 7 shows that the composition having DM1 comprises at least 3 different components: DM0, DM1 and DM2.

FIG. 8 shows that the mixture of DM0 and DM2 comprises only these components. No DM1 is present.

Example 14 Synthesis of Iodine Functionalized Tri-Block Copolymers

This example details a method to covalently bond a radiopaque atom to a tri-block copolymer. The structure of a tri-block copolymer which is acylated is given below in formula (1).

Formula 1

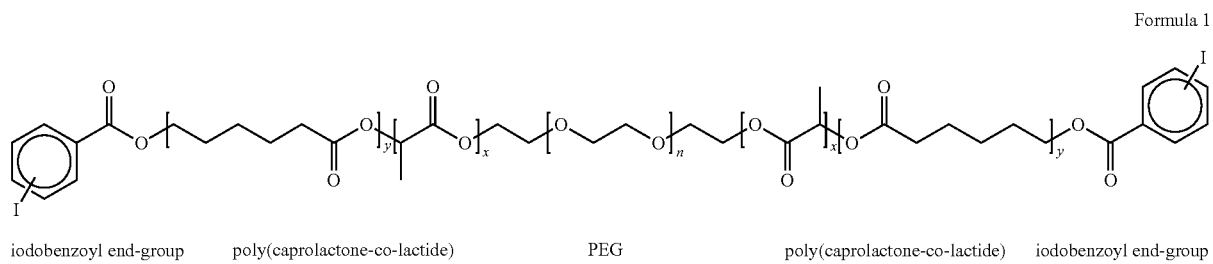

iodobenzoyl end-group    poly(caprolactone-co-lactide)    PEG    poly(caprolactone-co-lactide)    iodobenzoyl end-group The synthesis of tri-block copolymers wherein at least part of the hydroxyl end-groups of the tri-block copolymer are covalently bound to a compound containing radiopaque atoms was done according to the method previously described in U.S. Pat. No. 7,740,877, examples 1, 2 and 3. The synthesis led to tri-block copolymers (Table 9) with triiodobenzoyl groups (1.8 groups per chain) as confirmed by 1H NMR.

TABLE 9

Tri-block copolymers used.

| ID | ID | PLCA/PEG | Caprolactone/lactide | Degree of acylation | End-group | Number average mol. weight PEG |
|---|---|---|---|---|---|---|
| P (#81) | I-Gell ® #1 | 1.8 | 9/1 | 1.8 | Triiodo-benzoyl | 1500 |
| Q (#29) | I-Gell ® #2 | 1.0 | 9/1 | 1.8 | Triiodo-benzoyl | 1500 |

In the following examples different compositions comprising P and Q were made and the compositions are summarized in Table 10.

TABLE 10

Overview of compositions used in examples 15-19

| | Tri-block copolymer (wt %) | | |
|---|---|---|---|
| Example | P | Q | 17 |
| 15 | — | — | 100 |
| 16 | 25 | — | 75 |
| | 30 | — | 70 |
| | 50 | — | 50 |
| | 70 | — | 30 |

TABLE 10-continued

Overview of compositions used in examples 15-19

| Example | Tri-block copolymer (wt %) | | |
|---|---|---|---|
| | P | Q | 17 |
| 17 a | 30 | — | 70 |
| b | — | 30 | 70 |
| 18 a | — | — | 100 |
| b | 25 | — | 75 |
| 19 a | 25 | — | 75 |
| b | 50 | — | 50 |

Example 15 Loading of a Tri-Block Copolymer Composition with Contrast Agent Hexabrix™

In order to achieve prolonged release of a pharmaceutically active ingredient, retention in the treatment location (for example a joint) must be maintained for a minimum of 4 weeks. To determine this retention time the tri-block copolymer composition must be visualized. This example shows how loading a tri-block copolymer with a conventional contrast agent does not achieve this goal.

Polymer #17 (see Table 1) was loaded with 15% Hexabrix™ (Guerbet). Hexabrix™ contrast agent is a low osmolar ionic dimer. Each milliliter contains 393 mg of ioxaglate meglumine, 196 mg of ioxaglate sodium and 0.10 mg of edetate calcium disodium as a stabilizer. The solution contains 3.48 mg (0.15 vmEq) sodium in each milliliter and provides 32% (320 mg/mL) organically bound iodine.

The commercially available Hexabrix™ solution was diluted with phosphate buffer (50 mM phosphate, pH 7.4, 0.07 mM NaCl) at a ratio 15/85 v/v. This diluted Hexabrix™ solution was used to dissolve the polymer, leading to the preparation of a formulation containing 25 wt % polymer with respect to buffer and Hexabrix™. Each gram of formulation contained 44 mg ioxaglate meglumine.

The loaded tri-block copolymer composition was injected into a chicken knee and visualized using microCT (Skyscan model 1076, Skyscan, Kontich, Belgium) Scans were performed using the following scanner settings: isotropic voxelsize of 35 mm, at a voltage of 55 kV, a current of 170 mA, field of view of 35 mm, and a 0.5 mm aluminium filter, over 198° with a 0.8 rotation step. 1 hour after injection the visibility of the gel was diminished and a further 1 day later the composition could not be visualized. Make table T=0-1-24 hrs showing 100%-50%-0% visualization as relative grey value The results are also indicated in Table 11.

TABLE 11 retention of Polymer #17 (25% w/w) loaded with 15% Hexabrix

| Time point in hours | Relative grey surface area |
|---|---|
| T = 0 | 100% |
| T = 1 | 50% |
| T = 24 | 0% |

Example 16 Radiopaque Tri-Block Copolymer Compositions

This example shows that a tri-block copolymer wherein at least part of the hydroxyl end-groups of the tri-block copolymer are covalently bound to a compound containing radiopaque atoms can be visualized by microCT. (Skyscan model 1076, Skyscan, Kontich, Belgium) Scans were performed using the following scanner settings: isotropic voxelsize of 35 mm, at a voltage of 55 kV, a current of 170 mA, field of view of 35 mm, and a 0.5 mm aluminum filter, over 198° with a 0.8 rotation step. Scan time was 10 minutes. In this example different compositions were prepared comprising different weight percentages of tri-block copolymers (Table 10, example 16) wherein the hydroxyl end-groups of the tri-block copolymer are at least partially acylated with an acetyl group or wherein at least part of the hydroxyl end-groups of the tri-block copolymer are covalently bound to a compound containing radiopaque atoms.

The compositions (Table 10, examples 16) were prepared as follows. Both polymers P and #17 were separately dissolved in ethylacetate at a concentration of 500 mg/mL. The solutions were mixed at the desired ratios and the mixtures were transferred into petri dishes. The solvent was removed under nitrogen flow for 48 hours. To 500 mg polymer blend, phosphate buffer (50 mM, 0.07 mM NaCl, 0.02% NaN3, pH 7.4) was added to yield solutions at 25 wt %. The compositions were measured in glass vials and the X-ray intensity plotted on a graph (FIG. 8). The compositions were measured in glass vials and the X-ray intensity plotted on a graph (FIG. 8).

Example 17 CT Imaging in Radiopaque Tri-Block Copolymer Compositions

This example shows the CT visualization times for different mixtures of tri-block copolymers.

The mixtures of copolymers (Table 10, example 17a and 17b) were prepared, injected into the knee of a rat cadaver and visualized by microCT (Skyscan model 1076, Skyscan, Kontich, Belgium). Scans were performed using the following scanner settings: isotropic voxelsize of 35 mm, at a voltage of 55 kV, a current of 170 mA, field of view of 35 mm, and a 0.5 mm aluminum filter, over 198° with a 0.8 rotation step. The results are shown in Table 14.

The composition 17a was visible for only a few days whereas composition 17b was visible for 3 weeks (FIG. 11).

Example 18 Release Profiles of Tri-Block Copolymers Wherein the End Groups are Acylated or are Radiopaque Substituted Acyl Groups This example illustrates the release profile of a pharmaceutically active ingredient from tri-block copolymer compositions and also the degradation profiles for tri-block copolymer compositions comprising a pharmaceutically active ingredient.

OAc-Gell (#17) and a mixture of a I-Gell®#1 (P) and OAc-Gell (#17) were prepared at 25 wt % in 50 mM phosphate buffer at pH 7.4, 0.42% NaCl and 0.05% NaN3. The loading of Celecoxib was 1.25 mg/mL. Release experiments were performed as per example 6 and at 37° C. in PBS buffer containing 0.2% Tween 80. Error bars represent standard error of the mean (n=6). The results are shown in FIG. 9 and summarized in Table 12.

TABLE 12

Overview release time and erosion profile for examples 18a and 18b.

| Example | Release time | Erosion time (solid content) |
|---------|--------------|------------------------------|
| 18a | 28 | 28 |
| 18b | 35 | 35 |

Wet weight=weight of the depots, as measured by decanting the PBS buffer and weighing the remaining gel, after which the original vial-weight is subtracted Dry weight=weight of the freeze dried depots after decanting of the buffer (i.e. polymer weight) and subtracting the weight of the vial Solid content=polymer concentration in the depots (dry weight/wet weight)

Example 19 Degradation Profile for Tri-Block Copolymer Compositions

This example shows the in vivo degradation profile for compositions of tri-block copolymers wherein at least part of the hydroxyl end-groups of the tri-block copolymer are covalently bound to a compound containing radiopaque atoms.

Compositions (Table 10, example 19a and 19b) were prepared were prepared by dissolving 25 wt % tri-block copolymer (comprising 75% P and 25% #17, or 50% P and 50% #17) in 75% PBS buffer, pH 7.4. 50 mM, 0.15% NaCl of the composition was injected subcutaneously into rats knees. The injected volume of 19b was then visualized and measured using 3D micro-CT imaging (Skyscan model 1076, Skyscan, Kontich, Belgium). The rats were anesthetized using Isoflurane and then placed in a custom made scanner bed, fixing the hind limb in an extended position. Scans were performed using the following scanner settings: isotropic voxel size of 35 mm, at a voltage of 55 kV, a current of 170 mA, field of view of 35 mm, and a 0.5 mm aluminum filter, over 198° with a 0.8 rotation step. The rat knees and subcutaneous depots were scanned on days 0, 1, 4 and 8 and after that weekly until the gel was no longer visible. The scan time was 16 minutes and a frame averaging of 3 was used. Images obtained using the uCT scanner were reconstructed using Skyskan analysis software. The datasets were segmented using a fixed attenuation threshold between air and subchondral bone. Subsequently, regions of interest were drawn around the patellar cartilage and attenuation and volume were calculated. The injected volume of 19a (non-radiopaque), was monitored through the skin with a measuring caliper. The results are shown in FIG. 10 and summarized in Table 13 and 14.

TABLE 13

Overview of erosion monitoring for examples 19a and 19b.

| | 19a | | 19b | |
|---|---|---|---|---|
| Day | Observations | Surface area/% | Observations | Surface area/% |
| 0 | Distinct oval shape, sharp edges | 100 | Higher intensity than for 19a | 100 |
| 4 | Sharp edges maintained | 80 | | 70 |
| 8 | Less sharp edges on interior side | 40 | | 65 |
| 14 | Fractured shape - small light spots in dark area | 10 | | 75 |
| 21 | Not visible | — | | 50 |
| 40 | — | — | Still visible | 40 |

Surface area=relative area with respect to surface area at t=0 (set to 100%)

TABLE 14

Overview of compositions and microCT characteristics for examples 15-19

| | Tri-block copolymer (wt %) | | | Duration of visibility | Active |
|---|---|---|---|---|---|
| Example | P | Q | 17 | in micro CT | ingredient |
| 15 | — | — | 100 | <24 hours | Hexabrix ™ |
| 16 a | 25 | — | 75 | All visible in micro | — |
| | 30 | — | 70 | CT but duration | — |
| | 50 | — | 50 | of visibility | — |
| | 70 | — | 30 | not measured | — |
| 17 a | 30 | — | 70 | <7 days | — |
| b | — | 30 | 70 | ~4 weeks | — |
| 18 a | — | — | 100 | — | Celecoxib |
| b | 25 | — | 75 | — | Celecoxib |
| 19 a | 25 | — | 75 | ~40 days | — |
| b | 50 | — | 50 | ~77 days | — |

DISCUSSIONS AND CONCLUSIONS

As can be seen in FIG. 1, viscoelastic hydrogels were formed for compositions with more than 50% w/w of the C6-acylated PLCA-PEG-PLCA (II), i.e. the storage modulus (G') exceeds the loss modulus (G"). Interestingly, the addition of C6-acylated PLCA-PEG-PLCA led to considerable increase in hydrogel strength as demonstrated by a 10-fold increase of the moduli. This indicates that the micelle interactions, i.e. bridging between the micelles which hold together the network structure became stronger by addition of C6-acylated PLCA-PEG-PLCA. This characteristic shows that the rheology/mechanical strength of the mixture can be tuned using the teaching of the invention.

As can be seen in FIG. 2, viscoelastic hydrogels were formed for compositions with at least 50% w/w of the C12-acylated PLCA-PEG-PLCA (III), i.e. the storage modulus (G') exceeds the loss modulus (G"). Interestingly, the addition of C12-acylated PLCA-PEG-PLCA led to considerable increase in hydrogel strength as demonstrated by a 10-fold increase of the moduli. This indicates that the micelle interactions, i.e. bridging between the micelles which hold together the network structure became stronger by addition of C12-acylated PLCA-PEG-PLCA.

FIG. 3 shows that the degradation profile of the blends expressed as wet-gel weight loss, and these same samples are evaluated for their release profile of celecoxib as described in FIG. 4. By blending the same block co polymers with or without C6 end-groups in different ratio's, the formulated gels with drugs and buffer can be tuned to produce a burst release, or not, and they can be tuned to degrade over longer or shorter periods of time. By using C12-endgroups, the same ratio with non-endcapped produces a remarkable higher burst with shorter overall degradation and release time than the C6-endcapped comparable. These results are very interesting for use in chronic drug treatment where multiple injections are needed over the course of time, and where it is advantageous that the polymer is fully degraded shortly after the end of the release of the active pharmaceutical ingredient. So, the degradation profile (burst, speed, total disappearance) of the tri-block copolymer may be tuned using the teaching of the invention.

In FIG. 4, the cumulative release profile of celecoxib from 3 polymer mixtures is depicted. By varying the polymer end-modification and the type of end-group modification used, we are able to tune the release profile of celecoxib in terms of burst, release time and release rate from 25 to 50 days. It is highly beneficial to be able to tune the release profile in terms of total days of treatment, and the available drug dose per time unit. It is also very beneficial to be able to reduce the burst release to minimize side effects. In some applications one may choose to design a burst release in the first day (10-25% of total release), followed by a gradual dosing over an extended period of time, ie for use of cytostatic drugs in tumour eradication or anti-bacterial medication in case of infections.

As can be seen in FIG. 5, the cumulative release profile of celecoxib from the partially C6-modified PLCA-PEG-PLCA (DM 1.5) is similar in duration to the one of a blend fully C6-modified/unmodified PLCA-PEG-PLCA (75/25). However the gel prepared with the polymer mixture according to the invention showed a more regular release rate over that period of time.

As can be seen in FIG. 6 a tri-block copolymer composition with having a degree of modification of 1, has the same gelation temperature as measured by G', as a 50/50 mixture of tri-block copolymer compositions according to the invention containing DM0 and DM2 tri-block copolymers based on PLGA. We do observe a significant difference in G' between DM=1 (430 Pa) and mix of DM=2/DM=0 50-50 (300 PA). The result is shown in FIG. 6.

This shows that the simple mixing of two tri-block copolymers, wherein one of the two tri-block co-polymers has a degree of modification of 100% and one of the two tri-block copolymers has a degree of modification of 0% and wherein the two types of tri-block copolymers differ only on the degree of modification of the end group, exhibit the same physical properties as a tri-block composition with a defined degree of modification of 50%. However, the benefit of mixing is that one can work with a formulation comprising two fully characterized and easy to reproduce block-copolymers (DM=0 or DM=2), and with a mixing step that is easy to plan, execute and reproduce to those skilled in the art. In contrast to the aforementioned practice of the invention, the synthetic approach to achieve comparable DM always has a range of DM=0-1-2 block copolymers, which is more difficult to define, control and reproduce consistently within a pharmaceutical setting.

A tri-block copolymer loaded with Hexabrix™ can be used for imaging in microCT studies but the contrast agent diffuses out of the tri-block copolymer within 1 day thereby preventing prolonged imaging of the tri-block copolymer Table 11, example 15).

Surprisingly, a composition comprising a tri-block copolymer wherein at least part of the hydroxyl end-groups of the tri-block copolymer are covalently bound to a compound containing radiopaque atoms is suitable for microCT imaging over longer periods of up to time, as shown in example 16.

As summarized in Table 8, a composition comprising a tri-block copolymer wherein at least part of the hydroxyl end-groups of the tri-block copolymer are covalently bound to a compound containing radiopaque atoms maintains gel forming, gel erosion and controlled release properties whilst such composition can be visualized using micro CT.

From example 17 and FIG. 10, it is furthermore shown that it is possible to visualize a blend of a tri-block copolymer wherein the hydroxyl end-groups of the tri-block copolymer are at least partially acylated with an acetyl group or wherein at least part of the hydroxyl end-groups of the tri-block copolymer are covalently bound to a compound containing radiopaque atoms using micro CT, while maintaining gel forming, gel erosion and controlled release properties. In the given example 17 and FIG. 10, the blend of polymers with the same tri-block copolymer structure, but with different end-groups at 100% modification (namely tri-iodobenzoyl-group or acetyl-group), shows longer gel stability and longer release of the same hydrophobic compound than the pure 100% acetylated version. This is very beneficial for product development, for manufacturing, and at overall cost level, because it allows us to produce one type of tri-block copolymer at high levels of reproducibility, and subsequently fully modify it with two different end-groups at high reproducibility, then having these different variations fully characterized and qualified for animal and human uses, produce these on stock, and then by simply mixing these high quality products at different ratios, desired release profiles of pharmaceutically active ingredients can be obtained, also having different degradation profiles of the gel-depot, and making visualization of the depots possible in situ, or for other imaging purposes.

What is claimed is:

1. A composition, comprising:
    (a) an active ingredient,
    (b) a solvent and
    (c) a mixture of at least two types of tri-block copolymers of formula (1)

B-A-B          (1)

wherein B stands for a hydrophobic block, comprising at least one cyclic monomer selected from one or more of glycolide, lactide, ε-caprolactone, p-dioxanone (1,4-dioxan-2-one), trimethylene carbonate (1,3-dioxan-2-one), 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, 6-valerolactone, 3-methyl-1,4-dioxane-2,5-dione, 1,4-dioxane-2,5-dione, 6,6-dimethyl-dioxepan-2-one, 6,8-dioxabicycloctane-7-one and 5,5-dimethyl-1,3-dioxan-2-one,
    wherein A stands for a hydrophilic block, comprising a linear poly-(ethylene glycol) block having a number average molecular weight from 1000-2000 Da,
    i) wherein the mixture is prepared by mixing at least two types of tri-block copolymers of formula (1) having a degree of end-group modification of 100% and wherein the B-A-B types of tri-block copolymers differ only on the type of end-group or ii) wherein the mixture is prepared by mixing at least two types of tri-block copolymers of formula (1), wherein one of the at least two tri-block copolymers has a degree of end-group modification of 100% and one of the at least two tri-block copolymers has a degree of end-group modification of 0% and wherein the B-A-B types of tri-block copolymers differ only on the degree of modification of the end-groups; and where only tri-block copolymer with a degree of end-group modification of 100% or 0% has been added, and wherein the end-groups of the tri-block copolymer having an end-group modification of 100% are acylated with an acyl group represented by a compound of formula (2)

$$R^1\text{—}C(O)\text{—} \qquad (2)$$

wherein $R^1$ stands for an alkyl, alkenyl, alkynyl or aryl, wherein the $R^1$—C(O) group is covalently linked to the tri-block copolymer, and wherein the ratio of 100% end-group modified tri-blockcopolymer to 0% end-group modified tri-blockcopolymer ranges between about 75:25 and about 25:75, wherein a block ratio of the at least two tri-block copolymers, which block ratio is defined as the ratio between a sum of a number average molecular weight (Mn) of the B-blocks and a number average molecular weight (Mn) of the A-blocks ranges from 1.4 to 2.6, and wherein the composition shows controlled release of the active ingredient.

2. The composition according to claim 1, wherein the end-group of at least one of the two types of tri-block copolymer is covalently bound to a compound containing radiopaque atoms.

3. The composition according to claim 1, wherein B stands for a poly(lactide-co-ε-caprolactone) block.

4. The composition according to claim 1, wherein the acyl group is an acetyl group or a propionyl group.

5. The composition according to claim 3, wherein a weight ratio of E-caprolactone to lactide is at least 1/1.

6. The composition according to claim 1, wherein the solvent is water or an aqueous buffer solution.

7. The composition according to claim 1, wherein the composition is a pharmaceutical composition comprising a pharmaceutically active ingredient and further comprising a pharmaceutically acceptable adjuvant, carrier, excipient, contrast agent or dye.

8. A medicament comprising the composition according to claim 1.

9. A medicament capable of being injected through a needle of 18G or thinner including the composition according to claim 1.

10. A method for preparing a composition according to claim 1 suitable for forming a thermogel comprising the step of:

mixing at least two types of B-A-B types of tri-block copolymers of formula (1)

$$B\text{-}A\text{-}B \qquad (1).$$

11. A process for the preparation of a composition according to claim 1 comprising the steps of:

synthesizing the at least two types of tri-block copolymers and mixing the at least two types of tri-block copolymers with the active ingredient and the solvent.

12. A method for delivering a pharmaceutically active ingredient over an extended period to an animal requiring such treatment which comprises administering to such animal an effective amount of the composition of claim 1.

13. The composition according to claim 1, wherein the composition is a pharmaceutical composition further comprising a pharmaceutically acceptable adjuvant, excipient or carrier.

14. The composition according to claim 1, wherein the composition is a pharmaceutical composition further comprising a drug-encapsulating nano-particle or microparticle.

15. The composition according the claim 1, wherein the mixture of the at least two types of tri-block copolymers has a gel window between 30° C. and 50° C.

16. The composition according to claim 1, wherein the controlled release of the active ingredient is over a period of time of more than one day and up to six months when administered to an animal.

* * * * *